United States Patent [19]

Stevens et al.

[11] Patent Number: 5,317,085

[45] Date of Patent: May 31, 1994

[54] POLYNUCLEOTIDES THAT ENCODE THE HUMAN PROTEOGLYCAN PEPTIDE CORE OF THE EFFECTOR CELLS OF THE IMMUNE RESPONSE

[75] Inventors: Richard L. Stevens, Sudbury, Mass.; John H. Weis, Salt Lake City, Utah; Christopher F. Nicodemus, Franconia, N.H.

[73] Assignee: Brigham And Women's Hospital, Boston, Mass.

[21] Appl. No.: 909,644

[22] Filed: Jul. 7, 1992

Related U.S. Application Data

[60] Division of Ser. No. 635,544, Jan. 18, 1991, Pat. No. 5,171,674, which is a continuation-in-part of Ser. No. 224,035, Jul. 13, 1988, abandoned.

[51] Int. Cl.$^5$ .............................................. C07K 7/08
[52] U.S. Cl. .................................. 530/326; 530/806; 530/300
[58] Field of Search ............... 530/326, 327, 350, 380, 530/395, 838

[56] References Cited

FOREIGN PATENT DOCUMENTS

WO90/00606 1/1990 World Int. Prop. O. .

OTHER PUBLICATIONS

Shin et al (1985) Nature 317 445-448.
Luikart et al (1985) Blood 66: 866-872.
Coudron, C. et al., "Peptides with Alternating Serine and Glycine Residues as Substrate for Xylosyltransferase", Fed. Proc. Fed. Am. Soc. Exp. Biol.: 1641 (Abstract No. 346), (1980).
Trantravahi, R. V. et al., Proc. Natl. Acad. Sci. USA, 83:9207-9210 (1986).
Giacoletto, K. S. et al., J. Exp. Med., 164:1422-1439 (1986).
Bourdon, M. A. et al., Proc. Natl. Acad. Sci. USA, 82:1321-1325 (1985).
Stevens, R. L. et al., The Journal of Biological Chemistry, 260:14194-14200 (1985).
Avraham, S. et al., Proc. Natl. Acad. Sci. USA, 86:3763-3767 (1989).
Bourdon, M. A. et al., Molecular and Cellular Biology, 7:33-40 (1987).
Luikart, S. D. et al., Chemical Abstracts, 103:647, Abstract No. 212337K (1985).
Tantravahi, R. V. et al., Fed. Proc., 45:626, Abstract No. 2740 (1986).
Hassell, J. R. et al., Ann. Rev. Biochem., 55:539-567 (1986).
Krusius, T. et al., Proc. Natl. Acad. Sci. USA, 83:7683-7687 (1986).
T. F. Bumol and R. A. Reisfeld, Proc. Natl. Acad. Sci. USA, 79:1245-49 (1982).
Rettig, J. et al., Science, 231:1281-1884 (1986).
Stevens, R. L., "Intracellular Proteoglycans in Cells of the Immune System", in Biology of Proteoglycans, Academic Press, Inc., (1987), pp. 367-385.
Razin, E. et al., J. Biol. Chem., 257(12):7229-7236 (1982).
Levi-Schaffer, F. et al., Proc. Natl. Acad. Sci. USA, 83:6485-6488 (1986).
Stevens, R. L. et al., J. Immunol., 133(5):2674-2680 (1984).

Primary Examiner—Charles L. Patterson, Jr.
Assistant Examiner—Gabriele E. Bugaisky
Attorney, Agent, or Firm—Sterne, Kessler, Goldstein & Fox

[57] ABSTRACT

This invention relates to the identification, characterization, and sequencing of genetic sequences of human secretory granule proteoglycan peptide core protein, recombinant DNA clones directed against this sequence and against the sequence of the antisense RNA, and antibodies which recognize the native human secretory granule proteoglycan.

2 Claims, 9 Drawing Sheets

OTHER PUBLICATIONS

Bourdon, M. A. et al., *J. Biol. Chem.*, 261:12534–12537 (1986).

Berger, S. L. et al. (ed), *Methods In Enzymology*, 152: Academic Press (1987).

Stevens, R. L. et al. *J. Biol. Chem.*, 263:7287–7291 (1988).

Alliel, P. M. et al., *FEBS Lett.*, 236:123–126 (1988).

Perkins, A. S. et al., *Mol. Cel. Biol.*, 3:1123–1132 (1983).

Avraham, S. et al., *J. Biol. Chem.*, 264:16719–16726 (1989).

Perin, J. P. et al., *Biochem. J.*, 255:1007–1013 (1988).

Luikart, S. D. et al., *Cancer Res.*, 44:2907–2912 (1984).

Brennan, M. J. et al., *J. Biol. Chem.*, 259:13742–13750 (1984).

Stevens, R. L. et al., *Proc. Natl. Acad. Sci. USA*, 85:2284–2287 (1988).

Humphries, D. E. et al., *J. Biol. Chem.*, 267:13558–13563 (1992).

Avraham, S. et al., *J. Biol. Chem.*, 267:610–617 (1992).

Ghildyal, N. et al., *J. Biol. Chem.*, 267:8473–8477 (1992).

Gurish, M. F. et al., *J. Exp. Medicine*, 175:1003–1012 (1992).

Nicodemus, C. F. et al., *J. Biol. Chem.*, 265:5889–5896 (1990).

Razin, E. et al., *J. Immun.*, 132:1479–1486 (1984).

Reynolds, D. S. et al., *J. Biol. Chem.*, 263:12783–12791 (1988).

FIG. 2

```
1    GTGCAGCTGGGAGAGCTAGACTAAGTTGGTC ATG ATG CAG AAG CTA CTC AAA TGC          8
                                    M   M   Q   K   L   L   K   C

56   AGT CGG CTT GTC CTG GCT CTT GCC CTC ATC CTG GTT CTG GAA TCC TCA        24
     S   R   L   V   L   A   L   A   L   I   L   V   L   E   S   S

104  GTT CAA GGT TAT CCT ACG CAG AGA GCC AGG TAC CAA TGG GTG CGC TGC        40
     V   Q   G   Y   P   T   Q   R   A   R   Y   Q   W   V   R   C
                  XmoI

152  AAT CCA GAC AGT AAT TCT GCA AAC TGC CTT GAA GAA AAA GGA CCA ATG        56
     N   P   D   S   N   S   A   N   C   L   E   E   K   G   P   M

200  TTC GAA CTA CTT CCA GGT GAA TCC AAC AAG ATC CCC CGT CTG AGG ACT        72
     F   E   L   L   P   G   E   S   N   K   I   P   R   L   R   T

248  GAC CTT TTT CCA AAG ACG ATC CAG GAC TTC AAT CGT ATC TTC CCA            88
     D   L   F   P   K   T   I   Q   D   F   N   R   I   F   P

296  CTT TCT GAG GAC TAC TCT GGA AGT TCA GGC TTC CTA ACG GGC TCC TCT       104
     L   S   E   D   Y   S   G   S   S   G   F   L   T   G   S   S

344  GGA TCA GGA TCT GGG GAG AGT GAT GCT TTC CAT GAC AAC CTT AGG TCT CTT   120
     G   S   G   S   G   E   S   D   A   F   H   D   N   L   R   S   L
                       AccI

392  CAA CTA GTA GAC AGC AGC CAG GAC TTG GGT CAA CAT GGA TTA               136
     Q   L   V   D   S   S   Q   D   L   G   Q   H   G   L

440  GAC AGG AAT CTG CCC TCA GAC AGC CAG GAC TTG GGT CAA CAT GGA TTA       152
     D   R   N   L   P   S   D   S   Q   D   L   G   Q   H   G   L

488  GAA GAG GAT TTT ATG TTA TAA AAGAGGATTTTCCCACCTTGACACCAGGCAATGTA       158
     E   E   D   F   M   L   ***

544  GTTAGCATATTTTATGTACCATGGTTATATGATTAATCTTGGGACAAAGAATTTTATAGAAAT
607  TTTTAAACATCTGAAAAAGAAGCTTAAGTTTATCATCCTTTTTTT(T)CTCAT
```

-621 GCCACTGCTCTCCAGCTGGGTGACAGAGTGAGACTCCATCTCAAAAAAAAAAAAAAAAAA
-557 AAAAAGAAAGAAAAAGAAAAAGAAAAAGAAGAAAAAGAAGAAAAGTGTTCAGTCTTTGAAGGTTAGAGCTCAGC
-479 TTTGAAGTTTCACTTCACGAGCTTGGCTCAGTGAAATCTGAAATCCATTCTCTGAAGGTTAGAGCTCAGC
-401 ATGTTGAAGTTTGCTTAGATTGGTGACGAGCTTGGCTCAGTGAAATCTGAAATCCATTCTCTGAAGGAATGTTTT
-323 AGCAATCTAGTATTTAGATGTTACCTAAAGGCAGCAAGAATGTATGCTTGGCGAGGATATGTCCCCGTTACTCCATCCGACACTCATCTGAAGGAATGTTT
-246 GAAAAAAAATGTATGTCTTGCAGGCAACAAGAATGTATCCTGGCCAAGAATGTATCCCCGTTACTCCATCCGACACTCATCTGAAGG
-168 TTCATAATGGGTATGATGTCTTGCAGGCAACAAGAATGTATCCCCGTTACTCCATCCGACACTCATCTGAAGG
-89 CTATTTGTTCAGGAAATTGTGTAGTTCTGGGCGTGTGTTCTGTTGTTACTGTTCTGTGTAGCAGGGAACATTTCTAAAAGGGACAGAGAG start
                                                                    ATG ATG
                                                                    Met Met
                                                                     1
-11  CACCCTGCTACATTTCCTAATCAAGAAGTTGGCGTGCAGCTGGACGTAGACTAAGTGGGTC
                                                                  |—exon 1

CTG GTT CTA CTC AAA TGC AGT CGG CTT GTC GCT CTT ATC
Leu Val Leu Leu Lys Cys Ser Arg Leu Val Ala Leu Ile
        20

Gln Lys Leu Leu Lys Cys Ser Arg Leu Val Ala Leu Ile
CAG AAG CTA CTC AAA TGC AGT CGG CTT GTC GCT CTT ATC

-(~8 kb)-tacttagtaacaatgtgggtcctccgggca aagactcaggagtcttgttcccagccatctc

|—exon 2
CAA AAA CCA ATG TTC GAA CTA CCA CTT CCA GGT GAA TCC CTT
Gln Lys Pro Met Phe Glu Leu Pro Leu Pro Gly Glu Ser Leu
                                            exon 2—|
                                               60

GAA AAA GGA CCA ATG TTC GAA CTA CCA CTT CCA GGT GAA TCC CTT
Glu Lys Gly Pro Met Phe Glu Leu Leu Pro Gly Glu Ser Asn

TAC CAA TGG GTG CGC TGC AAT CCA GAC AGT AAT TCT GCA CAG AAC TGC CTT
Tyr Gln Trp Val Arg Cys Asn Pro Asp Ser Asn Ser Ala Gln Asn Cys Leu
             40                                                    50

CCC CGT CTG AGG ACT GAC CTT TTT CCg taagtggacttttctctaattaatt
Ile Pro Arg Leu Arg Thr Asp Leu Phe Pro
                              70

FIG. 4

-(~6 kb)-tccactggttttcccattttcttcatactc aga┤-exon 3
                                      (Pro) Lys Thr Arg Ile Gln Asp
                                           AAG ACG AGA ATC CAG GAC
                                                           80

TTG AAT CGT ATC TTC CCA CTT TCT GAG GAC TCT GGA TCA GGC TTC CTA ACG
Leu Asn Arg Ile Phe Pro Leu Ser Glu Asp Ser Gly Ser Gly Phe Leu Thr

GGC TCC GGC TCC GGA GGA GGA AGT GGG TAC
Gly Ser Gly Ser Gly Gly Gly Ser Gly Try
100                                  110

GAA ATG GAG CAG GAT TAC CAA CTA GTA GAC GAA GAA TCT GGA
Glu Met Glu Gln Asp Try Gln Leu Val Asp Glu Glu Ser Gly
            120

AAC CTT AGG TCT CTT GAC AGG AAT CTG CCC TCA GAC GAT GCT TTC
Asn Leu Arg Ser Leu Asp Arg Asn Leu Pro Ser Asp Asp Ala Phe
                                 140

GAC CAA CAT GGA TTA GAA GAG GAT TTT ATG TTA TAA AAGAGGATTTC
Asp Gln His Gly Leu Glu Glu Asp Phe Met Leu stop
150                                158

CCACCTTGACACCAGGCAATGTAGTTAGCATATATTTATGTACCATGGTTATATGATTAATCTTGGGACAAAGAATTT
ATAGAAATTTTAAACATCTGAAAAGAAGCTTAAGTTTATCATCATCCTTTTCTTTTCTCATGAATTCTTAAGGATAT
GCTTTAATGCTGTATCTATCTATTGTTCTTGAAATACCTGCTTAAAATACCATATTTTTGGTATCTTTTCAGAAGATTATCA
GAATTAATTAGATTCCATGCCATAAAATGTCTTGAAATGGCTTAAGAATAGTTCAACCAACACATCATTAT
TGGCAGGTAATTAGATATTTCATACCTAAATTAAGACTCTGACTTGGAATTATATAATGATATGCCCCTTTTCTTATA
AAACAAAAAAATAAT

FIG.4(cont.)

```
-504  AATTCTAGCAGACTCTGGACGTTAACGGAGGACGCTCATCCTGGGGGGCTGAGAGCTCGGAATGTT
-429  CCCTGCTCTTGTGCCTGACTCTGTGCGCCCAGCTCTCTTGGATGTGCGAGCTCAGTTCTG
-354  GAACAGCTGAGTGCTTCCTCCTGTCTGTTAGATGTTACCTGAAGAGGAAGAGGTGCCTGAGCTTGACTT
-279  TTTGATGGGAAACTTTTTTTAAACATGAATTGTACCTGAAGAGATGGGCAGAGGGAAGGGGAAAGCTTTTTGGAAGAAAAGTGCTGATTCGACTT
-204  ACCACACAAGCAAACGCCTAGGGAGTCCCGGTATGAACAGCTTTGGAAAAAAAGAAAAAATAATA
-129  TTCTCTTTCTCTGGGGTTGAGATGGGAAGCCCTGTTCAGGGGTATGAACGTGTGTTCTTGGGCAG

-54   GGTCTGAGGTTTGGAACCTCTTTCTCAAAGGGGACAGAAAAGAGACCCCTGCTACATTTGCTAATCCAGAGAGGCTGA

GTGGAGCCGAGCTGGTCAGG
      ┌─────────────────────────────────────────────────────────────────────────┐
      │GCC TTC GTC CTG GTT TGG GGA TCT TCA GTG CAA Ggt                          │
      │ALA PHE VAL LEU VAL TRP GLY SER SER VAL GLN(GLY)                         │
      │                                              exon 1┘                    │

-(~8kb)- ggttccttgttcgcaca  ggt aagagaccaggatcttaatc-
                            (GLY)
                                 ┌─exon 2
      ┌─────────────────────────────────────────────────────────────────────────┐
      │ATG CAG GTT CCC GTC GGC AGC CTT GTC CTG GCT CTC                          │
      │MET GLN VAL PRO VAL GLY SER ARG LEU VAL LEU ALA LEU                      │
      │                                   exon 1┘                               │

CGC TGC AAA CCG AAT GGC TTT TTT GCG AAC TGC ATC GAG GAG AGA AGG TAC CAG TGG GTC
      ARG CYS LYS PRO ASN GLY PHE PHE ALA ASN CYS ILE GLU GLU ARG ARG TYR GLN TRP VAL

GAC CTA ATA GAT GAA TCC AAT AAC AAC GGC CCT CCC ATG AAT AAT CCT GTT TTg taa
      ASP LEU ILE ASP GLU SER ASN ASN ASN GLY PRO PRO MET ASN ASN PRO VAL (LEU)
                                                                    exon 2┘
```

FIG. 5 gtagactttcatcgat -(~4 kb)-tttttttctttgtattt agg ATG GAA GGA CCC TCA AAA GAT
                                              (LEU)MET GLU GLY PRO SER LYS ASP
                                          └─exon 3

TTC ATC TCC AAT TAT GAT GAC TAT GGG TCA GGT TCG GGC TCT GGC
PHE ILE SER ASN TYR ASP ASP TYR GLY SER GLY SER GLY SER GLY

TCT GGC TCG GGT TCC GGC TCC GGA AGT GGC TTC CTA GGT GAC ATG GAA TGG GAA TAC
SER GLY SER GLY SER GLY SER GLY SER GLY PHE LEU GLY ASP MET GLU TRP GLU TYR

CAG CCA ACA GAT GAA AGC AAT ATT GTC TAT TTC AAC TAT AAG CCT TTT GAC AGG ATT
GLN PRO THR ASP GLU SER ASN ILE VAL TYR PHE ASN TYR LYS PRO PHE ASP ARG ILE

CTC ACT GAG CAA AAC CAA GAC GAC GAT TTT ATT ATA TCA
LEU THR GLU GLN ASN GLN ASP ASP ASP PHE ILE ILE STOP

ATGTGACGGTCTCTGTCTCCCCACCTCCATGTGGAACAATGTATTCAGTAGTGTACCACGTTAAATGA
CCAGTCTCAGGATAAAGAGTTTTACAGAAAATTTAAATGCCTGAAATCCTTGAATCCTTGTTACCCTTC
CTCATTAACTCGTAAGGAATTATGCTTTAATGCACTATCTTGTTCTTGGAAAATGCCTCATTTATGT
GTATTGAATCAACATTTAAGAATTAAACACACCCCAATCTTTCAAAGCCATACTGGTTT
GAAAATTTAATTGATAGACAAGTTGATGAACAATCTTTCATACCTAAGTGTTCAGGAACCAACTCGCATTGT
GAATTACAAATATATTCCTTTATGTGATTAAAAGAAATAAAGTG

FIG.5 (cont.)

POLYNUCLEOTIDES THAT ENCODE THE HUMAN PROTEOGLYCAN PEPTIDE CORE OF THE EFFECTOR CELLS OF THE IMMUNE RESPONSE

The research underlining this invention was supported with Government funds; the Government has certain rights in this invention.

This application is a division of application Ser. No. 07/635,544, filed Jan. 18, 1991, now U.S. Pat. No. 5,171,674 (national phase of PCT/US/89/03051 with an International Filing Date of Jul. 13, 1989), which is a continuation-in-part of U.S. patent application Ser. No. 07/224,035, filed Jul. 13, 1988, now abandoned.

FIELD OF THE INVENTION

The present invention is directed to the purification of human secretory granule proteoglycan and production of the peptide core thereof by recombinant DNA technology. It is also directed to the production of antibodies against human secretory granule proteoglycan.

BRIEF DESCRIPTION OF THE BACKGROUND ART

Secretory granule proteoglycans comprise one of several families of mammalian proteoglycans, all of which are highly acidic macromolecules possessing at least one sulfated, glycosaminoglycan chain covalently bound to a peptide core. Tantravahi, R. V., et al., *Proc. Natl. Acad. Sci. U.S.A.* 83:9207 (1986). Various proteoglycan families have been proposed in the human based on differential reactivity to panels of monoclonal antibodies, differential peptide mapping after proteolytic treatment, different sizes after translation, and, in some cases, different amino acid sequences. They are further differentiated by their eventual location in the cell (e.g., intracellular, extracellular, and/or pericellular matrix) and by the nature of the carbohydrate residues attached to their peptide cores. For instance, proteoglycans that are localized to extracellular matrices appear to belong to a family that is distinct from the subfamily of more hydrophobic proteoglycans intercalated into the plasma membrane. Tantravahi, R. V., et al., supra.

Although there are at least 12 distinct proteins in the human that exist as proteoglycan peptide cores, the complete primary structure and/or chromosomal location of only a few of these proteoglycans are presently known and no gene has been isolated that encodes the complete peptide core of any proteoglycan.

A cDNA that encodes the dermatan sulfate proteoglycan peptide core that resides in the extracellular matrix around fibroblasts has been cloned from a human embryonic fibroblast cell line. Krusius, T., and Ruoslahti, E., *Proc. Natl. Acad. Sci., U.S.A.* 83:7683 (1986). Its nucleotide sequence predicts a peptide core of 40,000 $M_r$ with three potential glycosaminoglycan initiation sites and three potential sites for N-linked oligosaccharides.

Cell surface glycoproteins may also exist as proteoglycans. For example, the transferrin receptor and the invariant chain of the class II antigens have been reported to be proteoglycans on the plasma membrane of human skin fibroblasts and human lymphoid tissues, respectively. Giacoletto, K. S., et al., *J. Exp. Med.* 164:1422 (1986). The deduced amino acid sequence of the cDNAs that encode the transferrin receptor and the invariant protein have revealed serine-glycine glycosaminoglycan initiation sites. Another proteoglycan which contains chondroitin sulfate glycosaminoglycans has been described on the surfaces of human melanoma cells. Bumol, T. F., and Ricefeld, R. A., *Proc. Natl. Acad. Sci. U.S.A.* 79:1245-1249 (1982). The gene that encodes its more than 240,000 $M_r$ peptide core is predicted to reside on chromosome 15. Rettig, W. J., et al., *Science* 231:1281 (1986).

The first clear evidence for the existence of proteoglycans stored within the granules of a cell was obtained from studies of the rat skin mast cell. However, it has become increasingly apparent that a number of cells which participate in immune and inflammatory responses, including mucosal mast cells, basophils, eosinophils, neutrophils, macrophages, platelets, and natural killer cells, also contain proteoglycans in their granules. The presence of a family of proteoglycans that resides inside cells rather than on the plasma membrane or in the extracellular matrix suggests that these molecules may be important in the functions of such cells for tumor surveillance and host defense against bacterial, viral, fungal, and parasitic pathogens. Stevens, R. L., "Intracellular Proteoglycans in Cells of the Immune System," In: *Biology of Proteoglycans* (1987), herein incorporated by reference, reviews the evidence for the localization of the proteoglycans of mast cells, basophils, and natural killer cells within the secretory granule, the unique structural features of these proteoglycans, and their possible functions in the immune response.

In Bourdon et al., *Proc. Natl. Acad. Sci. U.S.A.* 82:1322 (1985), a rat chondroitin sulfate proteoglycan peptide core cDNA was identified and sequenced. The selection of the cDNA clone pPG-1 from a cDNA library prepared from L2 rat yolk sac tumor poly(A)+ mRNA was accomplished by using oligonucleotides derived from two regions of the $NH_2$-terminal protein sequence of the L2 proteoglycan. The use of oligonucleotides from two different parts of the $NH_2$-terminal amino acid sequence was essential for the identification of the desired cDNA clones. Several clones that hybridized with one or the other of the 17-mer oligonucleotides but not the 11-mer were obtained. One of these clones was partially sequenced. The resulting sequence did not have complete homology with the appropriate 17-mer probe and did not code for the $NH_2$-terminal peptide sequence of the proteoglycan.

The amino acid sequence inferred from the pPG-1 proteoglycan peptide core cDNA clone revealed the complete primary structure of the mature proteoglycan peptide core produced by this rat tumor cell. The proteoglycan peptide core coding region, identified on the basis of inferred amino acid sequence homology with the proteoglycan peptide core $NH_2$-terminal amino acid sequence, codes for a 104 amino acid core protein with a calculated molecular weight of 10,190 daltons.

The amino acid sequence of the rat L2 cell proteoglycan peptide core contains three structural regions beginning with a 14 amino acid $NH_2$-terminal region followed by a 49 amino acid serine-glycine repeat region and a 41 amino acid COOH-terminal region. The functions of the $NH_2$- and COOH-terminal regions are unknown, although it is thought that they play a role in determining interactions between the proteoglycan and both cell surfaces and extracellular molecules.

It is also thought that the function of the serine-glycine repeat region in the middle of the molecule is to serve as a recognition and receptor site for the attachment of chondroitin sulfate side chains. The attachment of chondroitin sulfate and heparin chains onto all proteoglycan cores is accomplished via O-glycosyl linkage to serine. Moreover, it is known that glycine residues are also involved in glycosaminoglycan attachment, since glycine is abundant in proteoglycans, and synthetic peptides containing alternating serine and glycine can serve as acceptors for glycosaminoglycan chain initiation. The extent of serine O-glycosylation in the L2 proteoglycan has been estimated to be near 60%, indicating that at least 14 of the serine residues of the core protein bear a chondroitin sulfate chain. Bourdon et al. noted that the structure of the serine-glycine region closely parallels that predicted for the glycosaminoglycan attachment region of a rat heparin proteoglycan, indicating that the serineglycine repeat may be a general feature of at least a subset of proteoglycans. Because the pronase-resistant glycosaminoglycan attachment region of rat mast cell heparin proteoglycan contains only serine and glycine amino acids, it was proposed that 15-20 serine residues alternate with glycine residues, with heparin chains being attached to at least two of every three serines. It would appear that at least two proteoglycans, the rat mast cell heparin proteoglycan and the rat yolk sac tumor proteoglycan, have identical or nearly identical glycosaminoglycan attachment regions. The codon usage for serine and glycine is quite restricted in the pPG-1 cDNA, with 81% of the serine residues being coded for by two of six possible codons and 70% of the glycine residues being coded for by one of its four possible codons.

In addition to chondroitin sulfate side chains, many other proteoglycans have O- and N-linked oligosaccharides. These oligosaccharide chains are linked to the proteoglycan peptide core through either threonine (serine) O-glycosyl or asparagine N-glycosyl acceptor recognition sequences. An examination of the rat L2 cell proteoglycan peptide core amino acid sequence does not reveal any asparagine oligosaccharide acceptor sites that have the sequence X-asparagine-Y-serine. Bourdon, M. A. et al., supra; Hughes, R. C., *Prog. Biophys. Mol. Biol.* 26:189-268 (1973).

In Stevens et al., *J. Biol. Chem.* 260:14194-14200 (1985), the applicant and several other investigators report an analysis of the structure of the protein of the intracellular chondroitin E proteoglycan from the interleukin 3-dependent mouse mast cell. The analysis revealed the sum of the glycine, serine, and glutamic acid/glutamine residues accounted for 70% of the total amino acids in the core peptide. The authors note that the mouse mast cell chondroitin sulfate E is similar to the rat serosal mast cell heparin proteoglycan in that both are packaged in secretory granules, are protease-resistant, and have highly sulfated glycosaminoglycans, and have peptide cores which are rich in serine and glycine. They also noted that the mouse chondroitin sulfate E proteoglycan has a peptide core somewhat similar to the chondroitin sulfate proteoglycan isolated by Bourdon et al., supra, from the rat yolk sac's tumor in size and in Ser, Gly, and Glx content.

Tantravahi et al., *Proc. Natl. Acad. Sci. U.S.A.* 83:9207-9210 (1986), reported on the use of the pPG-1 probe disclosed in Bourdon et al., supra, and subclones thereof to demonstrate that the same gene is expressed in mouse bone marrow derived mast cells (BMMC) (cells that contain intracellular chondroitin sulfate E proteoglycan) and rat serosal mast cells (cells that contain intracellular heparin proteoglycan).

SUMMARY OF THE INVENTION

The invention relates to the identification, characterization, and sequencing of cDNAs and genomic fragments which encode the secretory granule proteoglycan peptide core protein that is present in human promyelocytic leukemia cell line HL-60.

According to the invention, there are provided genetic sequences encoding human secretory granule proteoglycan peptide core protein. The invention also provides for expression vectors containing such genetic sequences, hosts transformed with such expression vectors, and methods for producing the genetically engineered or recombinant secretory granule proteoglycan peptide core protein.

The present invention also provides genetic sequences encoding human secretory granule proteoglycan peptide core protein antisense RNA, expression vectors containing such genetic sequences, hosts transformed with such expression vectors, methods for producing the genetically engineered or recombinant antisense RNA, and methods for the inhibition of expression of the human proteoglycan peptide core protein gene expression using these vectors.

The invention further provides antibodies which specifically recognize human secretory granule proteoglycan. The antibodies were raised against consensus polypeptides whose sequences are based on the consensus sequence of the cDNAs encoding this protein.

The secretory granule proteoglycan cDNA, recombinant protein, antisense RNA and antibodies provided by the invention are useful as diagnostic probes for monitoring the activation and involvement of immune effector cells in health and disease.

For example, because this proteoglycan is released from the human natural killer cell during its killing of tumor cells, the antibodies can be used in diagnosing and monitoring cancer. In another example, because this proteoglycan is also released by mast cells during immunologic activation, the antibodies can be used to monitor inflammation and allergic disorders. Further, because human secretory granule proteoglycan peptide core protein is expressed in the inflammatory response which accompanies tissue injury and repair and some immunological responses, antibodies raised against human secretory granule proteoglycan peptide core protein can be used in assays to detect, and follow the course of, such reactions in humans.

Different hematopoietic cells have different types of carbohydrate bound to this proteoglycan peptide core. However, because the peptide core of this family of proteoglycans will be the same in different human hematopoietic cells, the antibody of the invention will recognize all secretory granule proteoglycan peptide cores of hematopoietic effector cells.

The secretory granule proteoglycan interacts with proteases. When mast cell proteases are bound to this proteoglycan, their degradative activity against large substrates is greatly diminished. Therefore, they may also be useful in vitro and in vivo as specific proteolytic inhibitors.

DESCRIPTION OF THE FIGURES

FIG. 2. Consensus nucleotide sequence of the HL-60 cell-derived cDNAs and the predicted amino acid sequence of the translated proteoglycan peptide core. The arrow indicates the putative site of cleavage of the signal peptide. Stop codons are indicated by ***. The number on the right and left indicate the amino acid and the cleotide in the respective sequence. The XmnI and AccI restriction sites are indicated. The 5' end of the cDNA-H12 was 4 bp longer, and the 5' end of cDNA-H19 was 14 bp shorter than cDNA-H4. cDNA-H8 differed from the cDNA-H4 in that it had an extra thymidine (shown in parentheses) at the 3' end of its cDNA.

FIG. 4. Nucleotide sequence of the gene that encodes the peptide core of human secretory granule proteoglycans. The nucleotide sequences of the 5' flanking region, the exon/intron junctions, and the three exons are depicted. The hydrophobic signal peptide of the translated proteoglycan peptide core in exon I and the serine-glycine rich glycosaminoglycan attachment region in exon 3 are boxed. The polyadenylation site in exon 3 is underlined.

FIG. 5. Nucleotide sequence of the mouse gene that encodes the peptide core of mouse secretory granule proteoglycans. The nucleotide sequence of the 5' flanking region, the exon/intron junctions, and the three exons are depicted. The arrow indicates the probable transcription-initiation site. The hydrophobic signal peptide of the translated proteoglycan peptide core is boxed in exon 1. The di-acidic amino acid sequence that has been proposed to dictate glycosaminoglycan addition to proteins and the serine-glycine glycosaminoglycan attachment region are boxed in exon 3. The polyadenylation site in exon 3 is underlined.

BRIEF DESCRIPTION OF THE PREFERRED EMBODIMENTS

I. Definitions

Figure 1:
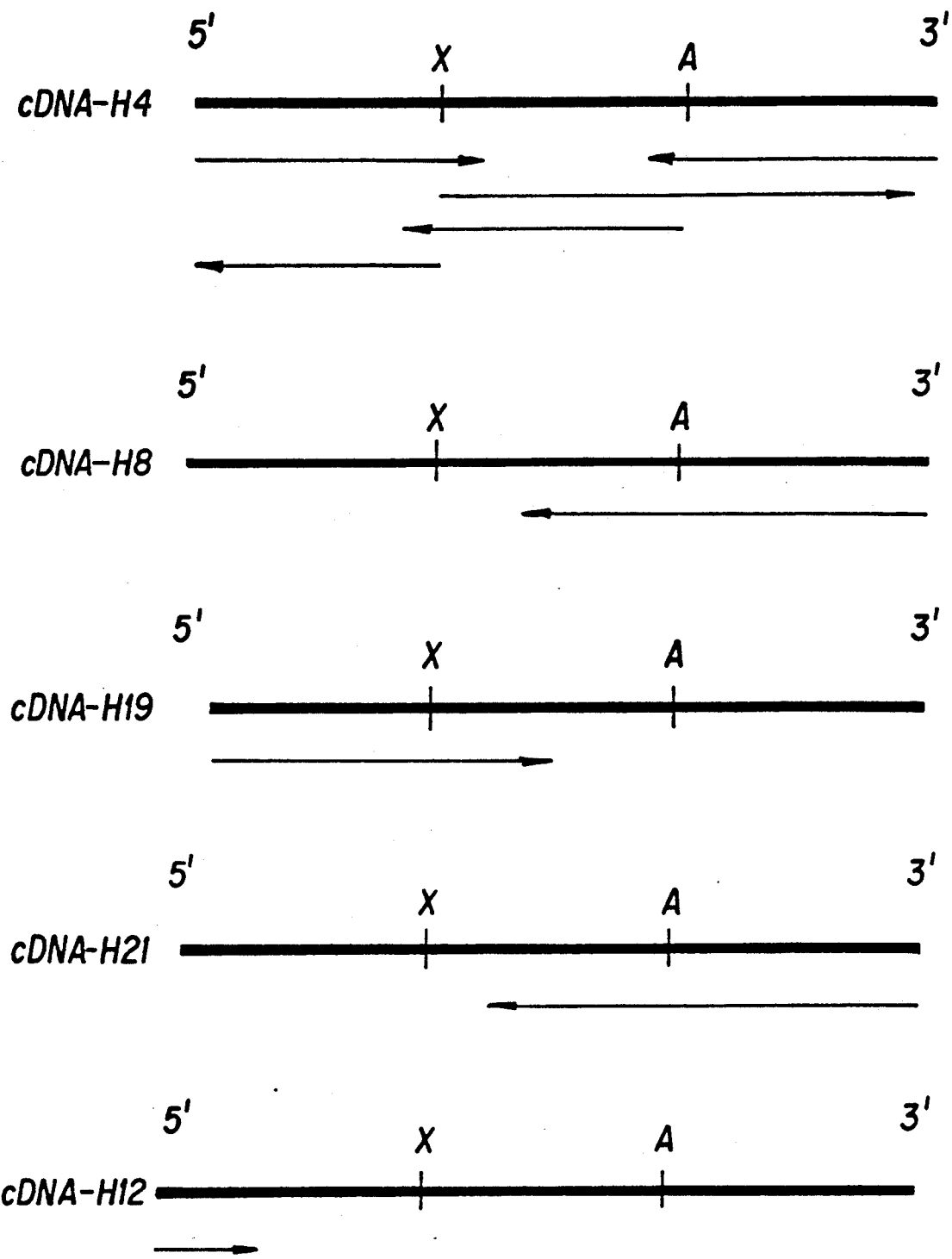
FIG. 1. Restriction map and nucleotide sequencing strategy of cDNA-H4 and its related cDNA. The cDNA-H4 originated from HL-60 cells and "X" and "A" refer to the sites within each cDNA which are susceptible to XmnI and AccI, respectively. The arrows indicate the direction and length of each subcloned fragment of cDNA that was sequenced.

In the description that follows, a number of terms used in recombinant DNA (rDNA) technology are extensively utilized. In order to provide a clear and consistent understanding of the specification and claims, including the scope to be given such terms, the following definitions are provided.

Gene. A DNA sequence containing a template for a RNA polymerase. The RNA transcribed from a gene may or may not code for a protein. RNA that codes for a protein is termed messenger RNA (mRNA) and, in eukaryotes, is transcribed by RNA polymerase II. However, it is also known to construct a gene containing a RNA polymerase II template wherein a RNA sequence is transcribed which has a sequence complementary to that of a specific mRNA but is not normally translated. Such a gene construct is herein termed an "antisense RNA gene" and such a RNA transcript is termed an "antisense RNA." Antisense RNAs are not normally translatable due to the presence of translational stop codons in the antisense RNA sequence.

A "complementary DNA" or "cDNA" gene includes recombinant genes synthesized by reverse transcription of mRNA and from which intervening sequences (introns) have been removed.

Cloning vehicle. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vehicle, and into which DNA may be spliced in order to bring about its replication and cloning. The cloning vehicle may further contain a marker suitable for use in the identification of cells transformed with the cloning vehicle. Markers, for example, are tetracycline resistance or ampicillin resistance. The word "vector" is sometimes used for "cloning vehicle."

Expression vehicle. A vehicle or vector similar to a cloning vehicle but which is capable of expressing a gene which has been cloned into it, after transformation into a host. The cloned gene is usually placed under the control of (i.e., operably linked to) certain control sequences such as promoter sequences. Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Proteoglycan. This term as used throughout the specification and claims means "human secretory proteoglycan" which may or may not contain glycosaminoglycan chains covalently bound to the proteoglycan's core protein. The term is also meant to include peptide fragments of human secretory proteoglycan wherein the peptide core protein contains less than the naturally-occurring number of amino acids, such as partial fragments of proteoglycan which retain biological (functional or structural) activity. An example of a functional activity is the ability to induce a specific biological response in the same manner that the native non-recombinant protein does. An example of a structural activity is the ability to bind antibodies which also recognize the native non-recombinant protein.

The term is also used to include any peptide which comprises the sequence of a naturally-occurring human secretory granule proteoglycan peptide core protein or an analog thereof together with one or more flanking amino acids, which show human secretory proteoglycan biological (functional or structural) activity.

The present invention pertains both to expression of full-length human secretory granule proteoglycan peptide core protein, and to the functional derivatives of this protein.

Functional Derivative. A "functional derivative" of human secretory granule proteoglycan peptide core protein is a protein which possesses a biological activity (either functional or structural) that is substantially similar to a biological activity of non-recombinant human secretory granule proteoglycan. A functional derivative of human secretory granule proteoglycan peptide core protein may or may not contain post-translational modifications such as covalently linked carbohydrate, depending on the necessity of such modifications for the performance of a specific function. The term "functional derivative" is intended to include the "fragments," "variants," "analogues," or "chemical derivatives" of a molecule.

Fragment. A "fragment" of a molecule such as human secretory granule proteoglycan is meant to refer to any variant of the molecule, such as the peptide core, or a variant of the peptide core.

Variant. A "variant" of a molecule such as human secretory granule proteoglycan is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

Analog. An "analog" of a molecule such as human secretory granule proteoglycan is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art.

II. Genetic Engineering of Human Secretory Granule Proteoglycan

This invention comprises the amino acid sequence of human secretory granule proteoglycan peptide core protein, genetic sequences coding for the proteoglycan peptide core protein mRNA or antisense mRNA, expression vehicles containing the genetic sequences, hosts transformed therewith and recombinant human secretory granule proteoglycan peptide core protein and antisense RNA produced by such transformed host expression. The invention further comprises antibodies directed against the human secretory granule proteoglycan peptide core protein.

The process for genetically engineering human secretory granule proteoglycan peptide core sequences, according to the invention, is facilitated through the cloning of genetic sequences which are capable of encoding the peptide core and through the expression of such genetic sequences. As used herein, the term "genetic sequences" is intended to refer to a nucleic acid molecule (preferably DNA). Genetic sequences which are capable of encoding the peptide core of the human secretory granule proteoglycan are derived from a variety of sources. These sources include genomic DNA, cDNA, synthetic DNA, and combinations thereof. The preferred source of the genomic DNA or mRNA is the human promyelocytic leukemia cell line, HL-60.

The secretory granule proteoglycan peptide core protein genomic DNA of the invention may or may not include naturally occurring introns. Moreover, such genomic DNA may be obtained in association with the 5' promoter region of the human secretory granule proteoglycan peptide core protein gene sequences and/or with the 3' transcriptional termination region. Further, such genomic DNA may be obtained in association with the genetic sequences which encode the 5' non-translated region of the human secretory granule proteoglycan peptide core protein mRNA and/or with the genetic sequences which encode-the 3' non-translated region. To the extent that a host cell can recognize the transcriptional and/or translational regulatory signals associated with the expression of the mRNA and protein, then the 5' and/or 3' non-transcribed regions of the native gene, and/or, the 5' and/or 3' non-translated regions of the mRNA, may be retained and employed for transcriptional and translational regulation. Human secretory granule proteoglycan peptide core protein genomic DNA can be extracted and purified from any cell containing human chromosome 10 by means well known in the art (for example, see *Guide to Molecular Cloning Techniques,* S. L. Berger et al., eds., Academic Press (1987)).

Alternatively, human secretory granule proteoglycan peptide core protein mRNA can be isolated from any cell which produces or expresses human secretory granule proteoglycan, and used to produce cDNA by means well known in the art (for example, see *Guide to Molecular Cloning Techniques,* S. L. Berger et al., eds., Academic Press (1987)). Preferably, the mRNA preparation used will be enriched in mRNA coding for human secretory granule proteoglycan peptide core protein, either naturally, by isolation from a cells which are producing large amounts of the protein, or in vitro, by techniques commonly used to enrich mRNA preparations for specific sequences, such as sucrose gradient centrifugation, or both.

For cloning into a vector, such suitable DNA preparations (either human genomic DNA or cDNA) ire randomly sheared or enzymatically cleaved, respectively, and ligated into appropriate vectors to form a recombinant gene (either genomic or cDNA) library. A DNA sequence encoding human secretory granule proteoglycan peptide core protein or its functional derivatives may be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

Libraries containing human secretory granule proteoglycan peptide core protein clones may be screened and a human secretory granule proteoglycan peptide core protein clone identified by any means which specifically selects for human secretory granule proteoglycan peptide core protein DNA such as, for example, a) by hybridization with an appropriate nucleic acid probe(s) containing a sequence specific for the DNA of this protein, or b) by hybridization-selected translational analysis in which native mRNA which hybridizes to the clone in question is translated in vitro and the translation products are further characterized, or, c) if the cloned genetic sequences are themselves capable of expressing mRNA, by immunoprecipitation of a translated human secretory granule proteoglycan peptide core protein product produced by the host containing the clone.

Oligonucleotide probes specific for human secretory granule proteoglycan peptide core protein which can be used to identify clones to this protein can be designed from knowledge of the amino acid sequence of the protein's peptide core. The sequence of amino acid residues in a peptide is designated herein either through the use of their commonly employed three-letter designations or by their single-letter designations. A listing of these three-letter and one-letter designations may be found in textbooks such as *Biochemistry*, Lehninger, A., Worth Publishers, New York, N.Y. (1970). When the amino acid sequence is listed horizontally, the amino terminus is intended to be on the left end whereas the carboxy terminus is intended to be at the right end. The residues of amino acids in a peptide may be separated by hyphens. Such hyphens are intended solely to facilitate the presentation of a sequence.

Because the genetic code is degenerate, more than one codon may be used to encode a particular amino acid (Watson, J. D., In: *Molecular Biology of the Gene*, 3rd Ed., W. A. Benjamin, Inc., Menlo Park, Calif. (1977), pp. 356–357). The peptide fragments are analyzed to identify sequences of amino acids which may be encoded by oligonucleotides having the lowest degree of degeneracy. This is preferably accomplished by identifying sequences that contain amino acids which are encoded by only a single codon.

Although occasionally an amino acid sequence may be encoded by only a single oligonucleotide sequence, frequently the amino acid sequence may be encoded by any of a set of similar oligonucleotides. Importantly, whereas all of the members of this set contain oligonucleotide sequences which are capable of encoding the same peptide fragment and, thus, potentially contain the same oligonucleotide sequence as the gene which encodes the peptide fragment, only one member of the set contains the nucleotide sequence that is identical to the exon coding sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

Using the genetic code (Watson, J. D., In: *Molecular Biology of the Gene*, 3rd Ed., W. A. Benjamin, Inc., Menlo Park, Calif. (1977)), one or more different oligonucleotides can be Identified from the amino acid sequence, each of which would be capable of encoding the human secretory granule proteoglycan. The probability that a particular oligonucleotide will, in fact, constitute the actual human secretory granule proteoglycan encoding sequence can be estimated by considering abnormal base pairing relationships and the frequency with which a particular codon is actually used (to encode a particular amino acid) in eukaryotic-cells. Such "codon usage rules" are disclosed by Lathe, R., et al., *J. Molec. Biol*, 12:1–12 (1985). Using the "codon usage rules" of Lathe, a single oligonucleotide sequence, or a set of oligonucleotide sequences, that contain a theoretical "most probable" nucleotide sequence capable of encoding the human secretory granule proteoglycan sequences is identified.

The suitable oligonucleotide, or set of oligonucleotides, which is capable of encoding a fragment of the human secretory granule proteoglycan peptide core protein gene (or which is complementary to such an oligonucleotide, or set of oligonucleotides) may be synthesized by means well known in the art (see, for example, *Synthesis and Application of DNA and RNA*, S. A. Narang, ed., 1987, Academic Press, San Diego, Calif.) and employed as a probe to identify and isolate the cloned human secretory granule proteoglycan peptide core protein gene by techniques known in the art. Techniques of nucleic acid hybridization and clone identification are disclosed by Maniatis, T., et al, (In: *Molecular Cloning, A Laboratory Manual*, Cold Spring Harbor Laboratories, Cold Spring Harbor, N.Y. (1982)), and by Hames, B. D., et al. (In: *Nucleic Acid Hybridization, A Practical Approach*, IRL Press, Washington, D.C. (1985)), which references are herein incorporated by reference. Those members of the above-described gene library which are found to be capable of such hybridization are then analyzed to determine the extent and nature of the human secretory granule proteoglycan peptide core protein encoding sequences which they contain.

To facilitate the detection of the desired human secretory granule proteoglycan peptide core protein DNA encoding sequence, the above-described DNA probe is labeled with a detectable group. Such detectable group can be any material having a detectable physical or chemical property. Such materials have been well-developed in the field of nucleic acid hybridization and in general most any label useful in such methods can be applied to the present invention. Particularly useful are radioactive labels, such as $^{32}P$, $^{3}H$, $^{14}C$, $^{35}S$, $^{125}I$, or the like. Any radioactive label may be employed which provides for an adequate signal and has a sufficient half-life. The oligonucleotide may be radioactively labeled, for example, by "nick-translation" by well-known means, as described in, for example, Rigby, P. J. W., et al., *J. Mol. Biol.* 113:237 (1977) and by T4 DNA polymerase replacement synthesis as described in, for example, Deen, K. C., et al., *Anal. Biochem.* 135:456 (1983).

Alternatively, polynucleotides are also useful as nucleic acid hybridization probes when labeled with a non-radioactive marker such as biotin, an enzyme or a fluorescent group. See, for example, Leary, J. J., et al.,

*Proc, Natl. Acad. Sci. U.S.A.* 80:4045 (1983); Renz, M., et al., *Nucl. Acids Res.* 12:3435 (1984); and Renz, M., *EMBO J.* 6:817 (1983).

Thus, in summary, the actual identification of human secretory granule proteoglycan peptide sequences permits the identification of a theoretical "most probable" DNA sequence, or a set of such sequences, capable of encoding such a peptide. By constructing an oligonucleotide complementary to this theoretical sequence (or by constructing a set of oligonucleotides complementary to the set of "most probable" oligonucleotides), one obtains a DNA molecule (or set of DNA molecules), capable of functioning as a probe(s) for the identification and isolation of clones containing the human secretory granule proteoglycan gene.

In an alternative way of cloning the human secretory granule proteoglycan gene, a library is prepared using an expression vector, by cloning DNA or, more preferably cDNA prepared from a cell capable of expressing human secretory granule proteoglycan, into an expression vector. The library is then screened for members which express human secretory granule proteoglycan peptide core protein, for example, by screening the library with antibodies to the protein.

In another embodiment, a previously described rat L2 cell-derived cDNA to a related proteoglycan, PPG-1, disclosed in Bourdon et al., *Proc. Natl. Acad, Sci. U.S.A.* 82:1322 (1985) is used to identify a human cDNA or genomic sequence encoding secretory granule proteoglycan peptide core protein. For example, Southern blots of digested human genomic DNA may be probed with nick-translated pPG-1 or pPG-14 (a gene specific 489 bp Ssp I →3' end fragment of pPG-1), Tantravahi et al., *Proc, Natl. Acad, Sci. U.S.A.* 83:9207 (1986), under reduced stringency if necessary to allow for mismatch between the sequence expressed in the different species.

The above discussed methods are, therefore, capable of identifying genetic sequences which are capable of encoding the human secretory granule proteoglycan peptide core protein or fragments of this protein. In order to further characterize such genetic sequences, and, in order to produce the recombinant protein, it is desirable to express the proteins which these sequences encode. Such expression identifies those clones which express proteins possessing characteristics of human secretory granule proteoglycan. Such characteristics may include the ability to specifically bind human secretory granule proteoglycan antibody, the ability to elicit the production of antibody which are capable of binding to human secretory granule proteoglycan, the ability to provide an human secretory granule proteoglycan-associated function to a recipient cell, among others.

III Expression of Human Secretory Granule Proteoglycan and its Functional Derivatives To express human secretory granule proteoglycan peptide core protein, transcriptional and translational signals recognizable by an appropriate host are necessary. The cloned human secretory granule proteoglycan peptide core protein encoding sequences, obtained through the methods described above, and preferably in a double-stranded form, may be operably linked to sequences controlling transcriptional expression in an expression vector, and introduced into a host cell, either prokaryote or eukaryote, to produce recombinant human secretory granule proteoglycan peptide core protein or a functional derivative thereof. Depending upon which strand of the human secretory granule proteoglycan peptide core protein encoding sequence is operably linked to the sequences controlling transcriptional expression, it is also possible to express human secretory granule proteoglycan peptide core protein antisense RNA or a functional derivative thereof.

Expression of the proteoglycan peptide core protein in different hosts may result in different post-translational modifications which may alter the properties of the proteoglycan. Preferably, the present invention encompasses the expression of the human secretory granule proteoglycan peptide core protein, or a functional derivative thereof, in eukaryotic cells, and especially mammalian, insect and yeast cells. Especially preferred eukaryotic hosts are mammalian cells either in vivo, or in tissue culture. Mammalian cells provide posttranslational modifications to recombinant proteoglycan peptide core protein which include folding and/or glycosylation at sites similar or identical to that found for the native proteoglycan. Most preferably, mammalian host cells include rat-I fibroblasts, mouse bone marrow derived mast cells, mouse mast cells immortalized with Kirsten sarcoma virus, or normal mouse mast cells that have been co-cultured with mouse fibroblasts. Razin et al., *J. of Immun.* 132:1479 (1984); Levi-Schaffer et al., *Proc, Natl. Acad. Sci. (U.S.A.)* 83:6485 (1986) and Reynolds et al., "Immortalization of Murine Connective Tissue-type Mast Cells at Multiple Stages of Their Differentiation by Coculture of Splenocytes with Fibroblasts that Produce Kirsten Sarcoma Virus," *J Biol, Chem.* 263:12783–12791 (1988). See Example 5, below.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a human secretory granule proteoglycan peptide core protein encoding sequence and a promoter region sequence linked to the 5' end of the encoding sequence) are said to be operably linked if induction of promoter function results in the transcription of the human secretory granule proteoglycan peptide core protein encoding sequence mRNA and if the nature of the linkage between the two DNA sequences does not (1) result in the introduction of a frame-shift mutation, (2) interfere with the ability of the expression regulatory sequences to direct the expression of the human secretory granule proteoglycan mRNA, antisense RNA, or protein, or (3) interfere with the ability of the human secretory granule proteoglycan template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but shall in general include, as necessary, 5' non-transcribing and 5' non-translating (non-coding) sequences involved with initiation of transcription and translation respectively, such as the TATA box, capping sequence, CAAT sequence, and the like. Especially, such 5' nontranscribing control sequences will include a region which contains a promoter for transcriptional control of the operably linked gene.

Expression of the human secretory granule proteoglycan protein in eukaryotic hosts requires the use of regulatory regions functional in such hosts, and preferably eukaryotic regulatory systems. A wide variety of transcriptional and translational regulatory sequences can be employed, depending upon the nature of the eukaryotic host. The transcriptional and translational regulatory signals can also be derived from the genomic sequences of viruses which infect eukaryotic cells, such as adenovirus, bovine papilloma virus, Simian virus, herpes virus, or the like. Preferably,, these regulatory signals are associated with a particular gene which is capable of a high level of expression in the host cell.

In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell. Promoters from heterologous mammalian genes which encode mRNA product capable of translation are preferred, and especially, strong promoters such as the promoter for actin, collagen, myosin, etc., can be employed provided they also function as promoters in the host cell. Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); in yeast, the yeast gal4 gene promoter (Johnston, S. A., et al., *Proc. Natl. Acad. Sci. (U.S.A.)* 79:6971–6975 (1982); Silver, P. A., et al., *Proc. Natl. Acad. Sci. (U.S.A.)* 81:5951–5955 (1984)) or a glycolytic gene promoter may be used.

As is widely known, translation of eukaryotic mRNA is initiated at the codon which encodes the first methionine. For this reason, it is preferable to ensure that the linkage between a eukaryotic promoter and a DNA sequence which encodes the human secretory granule proteoglycan peptide core protein, or a functional derivative thereof, does not contain any intervening codons which are capable of encoding a methionine. The presence of such codons results either in a formation of a fusion protein (if the AUG codon is in the same reading frame as human secretory granule proteoglycan encoding DNA sequence) or a frame-shift mutation (if the AUG codon is not in the same reading frame as the human secretory granule proteoglycan encoding sequence).

If desired, a fusion product of the human secretory granule proteoglycan peptide core protein maybe constructed. For example, the sequence coding for human secretory granule proteoglycan peptide core protein may be linked to a signal sequence which will allow secretion of the protein from, or the compartmentalization of the protein in, a particular host. Such signal sequences may be designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of the operably linked genes can be modulated. Of interest are regulatory signals which are temperature-sensitive so that by varying the temperature, expression can be repressed or initiated, or are subject to chemical regulation, e.g., metabolite. Also of interest are constructs wherein both the human secretory granule proteoglycan peptide core protein mRNA and antisense RNA are provided in a transcribable forms but with different promoters or other transcriptional regulatory elements such that induction of human secretory granule proteoglycan peptide core protein mRNA expression is accompanied by repression of antisense RNA expression, and/or, repression of human secretory granule proteoglycan peptide core protein mRNA expression is accompanied by induction of antisense RNA expression.

Translational signals are not necessary when it is desired to express human secretory granule proteoglycan peptide core protein antisense RNA sequences.

If desired, the non-transcribed and/or non-translated regions 3' to the sequence coding for human secretory granule proteoglycan peptide core protein can be obtained by the above-described cloning methods. The 3'-non-transcribed region may be retained for its transcriptional termination regulatory sequence elements; the 3-nontranslated region may be retained for its translational termination regulatory sequence elements, or for those elements which direct polyadenylation in eukaryotic cells. Where the native expression control sequences signals do not function satisfactorily host cell, then sequences functional in the host cell may be substituted.

The vectors of the invention may further comprise other operably linked regulatory elements such as enhancer sequences, or DNA elements which confer tissue or cell-type specific expression on an operably linked gene.

To transform a mammalian cell with the DNA constructs of the invention many vector systems are available, depending upon whether it is desired to insert the human secretory granule proteoglycan peptide core protein DNA construct into the host cell chromosomal DNA, or to allow it to exist in an extrachromosomal form.

If the human secretory granule proteoglycan DNA encoding sequence and an operably linked promoter is introduced into a recipient eukaryotic cell as a non-replicating DNA (or RNA) molecule, which may either be a linear molecule or, more preferably, a closed covalent circular molecule which is incapable of autonomous replication, the expression of the human secretory granule proteoglycan protein may occur through the transient expression of the introduced sequence.

In a preferred embodiment, genetically stable transformants may be constructed with vector systems, or transformation systems, whereby human secretory granule proteoglycan peptide core protein DNA is integrated into the host chromosome. Such integration may occur de DNA within the cell or, in a most preferred embodiment, be assisted by transformation with a vector which functionally inserts itself into the host chromosome, for example, with retroviral vectors, transposons or other DNA elements which promote integration of DNA sequences in chromosomes. A vector is employed which is capable of integrating the desired gene sequences into a mammalian host cell chromosome.

Cells which have stably integrated the introduced DNA into their chromosomes are selected by also introducing one or more markers which allow for selection of host cells which contain the expression vector in the chromosome, for example the marker may provide biocide resistance, e.g., resistance to antibiotics, or heavy metals, such as copper, or the like. The selectable marker gene can either be directly linked to the DNA gene sequences to be expressed, or introduced into the same cell by co-transfection.

In another embodiment, the introduced sequence is incorporated into a plasmid or viral vector capable of autonomous replication in the recipient host. Any of a wide variety of vectors may be employed for this purpose, as outlined below.

Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, vaccinia virus, SV40, and, in yeast, plasmids containing the 2-micron circle, etc., or their derivatives. Such plasmids are well known in the art (Botstein, D., et al., *Miami Wntr. Symp.* 19:265-274 (1982); Broach, J. R., In: *The Molecular Biology of the Yeast Saccharomyces: Life Cycle and Inheritance,* Cold Spring Harbor Laboratory, Cold Spring Harbor, N.Y., p. 445-470 (1981); Broach, J. R., *Cell* 28:203-204 (1982); Bollon, D. P., et al., *J. Clin. Hematol. Oncol.* 10:39-48 (1980); Maniatis, T., In: *Cell Biology: A Comprehensive Treatise,* Vol, 3. Gene Expression, Academic Press, N.Y., pp. 563-608 (1980)), and are commercially available. For example, mammalian expression vector systems which utilize the MSV-LTR promoter to drive expression of the cloned gene, and in which it is possible to cotransfect with a helper virus to amplify plasmid copy number, and, integrate the plasmid into the chromosomes of host cells have been described (Perkins, A. S. et al., *Mol, Cell Biol.* 3:1123 (1983); Clontech, Palo Alto, Calif.).

Once the vector or DNA sequence containing the construct(s) is prepared for expression, the DNA construct(s) is introduced into an appropriate host cell by any of a variety of suitable means, including transfection. After the introduction of the vector, recipient cells are grown in a selective medium, which selects for the growth of vector-containing cells. Expression-of the cloned gene sequence(s) results in the production of the human secretory granule proteoglycan peptide core protein, or in the production of a fragment of this protein. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, affinity chromatography, electrophoresis, or the like.

The human secretory granule proteoglycan DNA encoding sequences, obtained through the methods above, will provide sequences which by definition, encode human secretory granule proteoglycan peptide core protein and which may then be used to obtain human secretory granule proteoglycan peptide core protein antisense RNA genetic sequences as the antisense RNA sequence will be that sequence found on the opposite strand of the strand transcribing the peptide core's mRNA. The antisense DNA strand may also be operably linked to a promoter in an expression vector such that transformation with this vector results in a host capable of expression of a human secretory granule proteoglycan antisense RNA in the transformed cell. Antisense RM and its expression may be used to interact with an endogenous human secretory granule proteoglycan peptide core DNA or RNA in a manner which inhibits or represses transcription or translation of the secretory granule proteoglycan peptide core gene in a highly specific manner. Use of antisense RNA probes to block gene expression is discussed in Lichtenstein, C., *Nature* 333:801-802 (1988).

IV. Construction and Identification of Antibodies to Human Secretory Granule Proteoglycan Peptide Core Protein In the following description, reference will be made to various methodologies well-known to those skilled in the art of immunology. Standard reference works setting forth the general principles of immunology include the work of Catty, D. (*Antibodies, A Practical Approach,* Vol. 1, IRL Press, Washington, D.C. (1988)); Klein, J. (*Immunology: The Science of Cell-Noncell Discrimination,* John Wiley & Sons, New York (1982)); Kennett, R., et al. (*Monoclonal Antibodies Hybridoma: A New Dimension in Biological Analyses,* Plenum Press, New York (1980)); Campbell, A. ("Monoclonal Antibody Technology," In: *Laboratory Techniques in Biochemistry and Molecular Biology,* Volume 13 (Burdon, R., et al., eds.), Elsevier, Amsterdam (1984)); and Eisen, H. N., (In: *Microbiology,* 3rd Ed. (Davis, B. D., et al., Harper & Row, Philadelphia (1980)).

An antibody is said to be "capable of binding" a molecule if it is capable of specifically reacting with the molecule to thereby bind the molecule to the antibody. The term "epitope" is meant to refer to that portion of a hapten which can be recognized and bound by an antibody. An antigen may have one, or more than one epitope. An "antigen" is capable of inducing an animal to produce antibody capable of binding to an epitope of that antigen. The specific reaction referred to above is meant to indicate that the antigen will react, in a highly selective manner, with its corresponding antibody and not with the multitude of other antibodies which may be evoked by other antigens.

The term "antibody" (Ab) or "monoclonal antibody" (Nab) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

The antibodies of the present invention are prepared by any of a variety of methods. For example, cells expressing human secretory granule proteoglycan peptide core protein, or a fragment thereof, can be administered to an animal in order to induce the production of sera containing polyclonal antibodies that are capable of binding human secretory granule proteoglycan. In a preferred method, a human secretory granule proteoglycan peptide core protein fragment is chemically synthesized and purified by HPLC to render it substantially free of contaminants. Such a preparation is then introduced into an animal in order to produce polyclonal antisera of high specific activity.

Monoclonal antibodies can be prepared using hybridoma technology (Kohler et al., *Nature* 256:495 (1975); Kohler et al., *Eur. J. Immunol,* 6:511 (1976); Kohler et al., *Eur. J. Immunol.* 6:292 (1976); Hamerling et al., In: *Monoclonal Antibodies and T-Cell Hybridomas,* Elsevier, N.Y., pp. 563-681 (1981)). In general, such procedures involve immunizing an animal with human secretory granule proteoglycan antigen. The splenocytes of such animals are-extracted and fused with a suitable myeloma cell line. Any suitable myeloma cell line may be employed in accordance with the present invention; however, it is preferable to employ the parent myeloma cell line (SP2O), available from the American Type Culture Collection, Rockville, Md. After fusion, the resulting hybridoma cells are selectively maintained in HAT medium, and then cloned by limiting dilution as described by Wands, J. R., et al., *Gastroenterology* 80:225-232 (1981), which reference is herein incorporated by reference). The hybridoma cells obtained through such a selection are then assayed to identify clones which secrete antibodies capable of binding the human secretory granule proteoglycan antigen.

Through application of the above-described methods, additional cell lines capable of producing antibodies which recognize epitopes of the human secretory granule proteoglycan protein can be obtained.

Antibodies against both highly conserved and poorly conserved regions of the human proteoglycan peptide core are useful for studies on the control of biosynthesis and catabolism of human secretory granule proteoglycans in normal and pathologic conditions. Further, these antibodies can be used clinically to monitor the progress of disease states wherein the expression of human secretory granule proteoglycan peptide core protein is aberrant.

The examples below are for illustrative purposes only and are not deemed to limit the scope of the invention.

EXAMPLE 1

Construction and Screening of a HL-60 cDNA Library. The promyelocytic leukemia cell line, HL-60, is a transformed human cell that synthesizes chondroitin sulfate proteoglycans and stores these proteoglycans in its secretory granules. Under certain in vitro conditions, this cell can be induced to differentiate into cells that resemble neutrophils, monocytes, macrophages, eosinophils, and basophils. HL-60 cells (line CCL 240; American Tissue Type Collection, Rockville, Md.) were lysed in the presence of guanidine isothiocynate (BRL, Gaithersburg, Md.), and total RNA was purified by the CsCl density-gradient centrifugation technique of Chirgwin et al., *Biochemistry* 18:5294 (1979). The poly (A)+ RNA that was obtained by oligo (dT)-cellulose (Collaborative Research, Waltham, Ma.) chromatography (Aviv, H., and Leder, P., *Proc. Natl. Acad. Sci.* U.S.A. 69:1408 (1972)) was converted into cDNA (Okakajama, H., and Berg, P., *Mol. Cell Biol.* 2:161-170 (1982)). The resulting cDNAs were blunt ended with T4 DNA polymerase (Biolabs, Beverly, Ma.), the internal EcoRI sites methylated, and the cDNAs ligated to EcoRI poly-linkers. After selection of cDNAs of >500 bp by Sepharose CL-4B (Phamacia) chromatography, the cDNAs were ligated to dephosphorylated λgt10 DNA. *Escherichia coli* (strain C600 Hfl) were infected with the resulting recombinant bacteriophages resulting in a library with a complexity $>1 \times 10^6$. The HL-60 cell-derived CDNA library was probed at 37° C. with [$\alpha$-$^{32}$P]dCTP (3000 Ci/mmol; New England Nuclear, Boston, Ma.) nicktranslated pPG-1 in hybridization buffer (50% formamide, 5×SSC (0.15M NaCl/15 mM sodium citrate), 2× Denhardt's buffer, 0.1% sodium dodecyl sulfate (SDS), 1 mM EDTA, 100 μg/ml salmon sperm DNA carrier, and 10 mM sodium phosphate). The filters were washed at 37° C. under conditions of low stringency of 1.0×SSC, 0.1% SDS, 1 mM EDTA, and 10 mM sodium phosphate, pH 7.0. Approximately 500,000 recombinants in the library were plated to isolate the clone designated cDNA-H4 (FIG. 1). The HL-60 cell-derived cDNA library (~500,000 recombinants) were rescreened using cDNA-H4 as the probe. Thirty clones that hybridized under conditions of high stringency (55° C.; 0.2×SSC, 1 mM EDTA, 0.1% SDS, and 10 mM sodium phosphate, pH 7.0) with cDNA-H4 were isolated from the secondary screening of the library.

The individual HL-60 cell-derived cDNAs and their subcloned fragments were inserted into M13mp18 and M13mp19 (Amersham, Arlington Heights, Ill.) and sequenced by the dideoxy chain termination method of Sanger et al., *Proc. Natl. Acad. Sci.* U.S.A. 74:5463 (1977). Both strands of cDNA-H4 were sequenced. The sequencing strategy is presented in FIG. 1. The consensus nucleotide sequence of the HL-60 derived secretory granule proteoglycan peptide core cDNAs is shown in FIG. 2.

A 249 bp EcoRI→EcoRI fragment has been isolated from a EcoRI digest of cDNA-HI9. The nucleotide sequence of this fragment (Table I) contains the sequence expected for a polyadenylation site (underlined) and the poly(A)+ tail (underlined). This fragment hybridizes to a genomic fragment that encodes the gene for this proteoglycan peptide core, and thus probably represents the last 249 bp of the transcript.

TABLE I

Consensus nucleotide sequence of the 3' end of the cDNA that encodes the peptide core of the HL-60 secretory granule proteoglycan (Avraham, S. et al., Proc. Natl. Acad. Sci. U.S.A. 86:3763-3767 (1989)).

GAATTCTTAA-AGGATTATGC-TTTAATGCTG-TTATCTATCT-TATTGTTCTT-GAAAATACCT-
GCATTTTTG-GTATCATGTT-CAACCAACAT-CATTATGAAA-TTAATTAGAT-TCCCATGGCC-
ATAAAATGGC-TTTAAAGAAT-ATATATATAT-TTTTAAAGTA-GCTTGAGAAG-CAAATTGGCA-
GGTAATATTT-CATACCTAAA-TTAAGACTCT-GACTTGGATT-GTGAATTATA-ATGATATGCC-
CCTTTTCTTA-TAAAAACAAA-AAAAAAATAA-T

EXAMPLE 2

Chromosomal Localization of the Human Gene that Encodes the Secretory Granule Proteoglycan Peptide Core of HL-60 Cells. For the chromosome localization of the human gene that encodes cDNA-H4, DNA from five different human/mouse (lines 13C2, 24B2, 1711, 462TG, and 175) and 12 different human/hamster (lines 35A2, 35A4, 35B5, 35C1, 35D3, 35D5, 35E4, 35F1, 3SF3, 35F5, 89E5, and 95A4) somatic cell hybrids were digested with BamHI. The resulting fragments were resolved by agarose gel electrophoresis, and the DNA blots were analyzed under conditions of high stringency using cDNA-H4 as a probe. The percent discordance of the cDNA-H4 probe to each human chromosome was determined as described in Table II; a discordant fraction of 0.00 indicates that, in HL-60 cells, the secretory granule proteoglycan peptide core gene is located on chromosome 10.

TABLE II

Segregation Pattern of cDNA-H4 with DNA from Human/Rodent Somatic Cell Hybrids

The DNA from different human/hamster and human/mouse somatic hybrid cell lines and the DNA from the controls were analyzed for their hybridization to cDNA-H4. The column designations are: +/+, both hybridization to cDNA/cDNA-H4 and the specific human chromosome are present; −/−, hybridization to the cDNA-H4 and the chromosome are both absent; +/−, hybridization is present but the chromosome is absent; and −/+, hybridization is absent but the chromosome is present. For calculation of the discordant fraction for each chromosome, the sum of the +/− and −/+ columns are divided by the sum of the +/+, −/−, +/− and −/− columns. The 19q+ category represents the der 19 translocation chromosomes for the hybrid clones derived from fusions with leukocytes from the two different X/19 translocation carriers. The X and Xq− categories represent the intact X and the der X translocation chromosomes. Bruns et al., Biochem Genet. 17:1031-1059 (1979).

| Human Chromosome | Segregation Pattern | | | | Discordant Fraction |
| --- | --- | --- | --- | --- | --- |
| | +/+ | −/− | +/− | −/+ | |
| 1 | 1 | 8 | 7 | 1 | 0.47 |
| 2 | 3 | 8 | 5 | 0 | 0.31 |
| 3 | 3 | 6 | 3 | 3 | 0.40 |
| 4 | 2 | 4 | 5 | 3 | 0.57 |
| 5 | 4 | 8 | 4 | 3 | 0.47 |
| 6 | 3 | 5 | 4 | 3 | 0.47 |
| 7 | 6 | 7 | 2 | 2 | 0.24 |
| 8 | 2 | 6 | 6 | 3 | 0.53 |
| 9 | 0 | 5 | 7 | 4 | 0.69 |
| 10 | 8 | 9 | 0 | 0 | 0.00 |
| 11 | 3 | 6 | 5 | 3 | 0.47 |
| 12 | 2 | 7 | 5 | 1 | 0.40 |
| 13 | 5 | 7 | 5 | 1 | 0.40 |
| 14 | 6 | 4 | 1 | 4 | 0.33 |
| 15 | 4 | 8 | 3 | 1 | 0.25 |
| 16 | 3 | 6 | 3 | 3 | 0.40 |
| 17 | 2 | 6 | 5 | 3 | 0.50 |
| 18 | 5 | 7 | 3 | 2 | 0.29 |
| 19 and 19q+ | 6 | 2 | 2 | 7 | 0.53 |
| 20 | 3 | 3 | 3 | 6 | 0.60 |
| 21 | 3 | 4 | 4 | 5 | 0.56 |
| 22 | 3 | 6 | 2 | 3 | 0.36 |
| X and Xq− | 2 | 4 | 6 | 4 | 0.63 |
| Y | 0 | 9 | 7 | 0 | 0.44 |

EXAMPLE 3

Identification of Nucleotide Sequences in the Human Genome that Encode Secretory Granule Proteoglycans and Related Proteins. The rat L2 cell-derived cDNA, pPG-1, disclosed in Bourdon et al., Proc. Natl. Acad. Sci. U.S.A. 82:1322 (1985) was used to identify the genomic fragments encoding human secretory granule proteoglycan peptide core protein from a BamHI digest of human genomic DNA. While no hybridization occurred when the DNA blot was probed under conditions of high stringency with either pPG-1 or pPG-M, or probed under conditions of low stringency with pPG-M, at least 10 DNA fragments were visualized when the blot was probed under conditions of low stringency with pPG-1. The large number of DNA fragments detected suggested that there was a multigene family in the human which contained repetitive sequences similar to those which encode the serine-glycine repeat region of the L2 cell proteoglycan peptide.

EXAMPLE 4

Isolation and Characterization of the Human Secretory Granule Proteoglycan Peptide Core Gene. Subcloned fragments of the HL-60 cell-derived proteoglycan cDNA, cDNA-H4, were radiolabeled with [α-$^{32}$P]dCTP (3000 Ci/mmol; DuPont-New England Nuclear) to a specific activity of $>10^8$ cpm/μg by either nick translation (Maniatis, T. et al., Molecular Cloning: A Laboratory Manual, Cold Spring Harbor Laboratory, Cold Spring Harbor, N.Y., pp. 109-114 (1985)) or random priming (Feinberg, A. P. et al., Annal. Biochem 166:224-229 (1983)), and then were used to screen $\sim 10^6$ recombinants in a EMBL3 human genomic library (Klickstein, L. B. et al., J. Exp. Ned. 165:1095-1112 (1987)) by plaque hybridization. Nitrocellulose filters (Millipore, Bedford, Ma.) were probed at 42° C. in 50% formamide, 0.75M NaCl, 75 mM sodium citrate, 5× Denhardt's buffer, 0.1% SDS, I mM EDTA, 100 μg/ml salmon sperm DNA carrier, and 10 mM sodium phosphate. The nitrocellulose filters were washed at 55° C. with 30 mM NaCl, 3 mM sodium citrate, 0.1% SDS, 1 mM EDTA, and 10 mM sodium phosphate, pH 7.0. Several independent clones were obtained using the entire 650 base pair (bp) HL-60 cell-derived cDNA, cDNA-H4. However, in order to obtain better representation of the 5′ flanking region of the gene, the human genomic library was rescreened using the 136 bp 5′→KpnI fragment of cDNA-H4 to isolate 2 additional clones. The restriction maps of the clones were determined by incubating samples of their DNA separately with AccI, BamHI, EcoRI, HindIII, KpnI, or SalI (New England Biolabs, Beverly, Ma). The digests were electrophoresed in 1% agarose gels, and the separated DNA fragments were transferred to Nytran membranes (Schleicher and Schuell, Keene, N.H.) (Southern, E. M., J. Mol. Biol. 98:503-517 (1975)). The resulting DNA blots were probed with specific 5′ (5′→KpnI and 5′→XmnI) and 3′ (XmnI→3′ and AccI→3′) fragments of cDNA-H4.

Nucleotide Sequence Analysis of the Human Secretory Granule Proteoglycan Gene. Human genomic fragments were subcloned into the Bluescript (Stratagene, La Jolla, Calif.) plasmid vector using double enzyme polarized shotgun ligations to improve the efficiency of recombination and to maintain the orientation of the subclones (Kurtz, D. T. et al., Gene 13:145-152 (1980)). Recombinant transformants were identified by colony hybridization and were restriction mapped by the same method as that used above for the phage clones. Double stranded DNA sequencing (Sanger, F. et al., Proc. Natl. Acad. Sci. U.S.A. 74:5463-5467 (1977); Zhang, H. et al., Nuc. Acid, Res. 16:1220-7 (1988)) was performed directly on the plasmid subclones using a Sequenase nucleotide sequencing kit (United States Biochemical, Cleveland, Ohio) and [α-$^{35}$S]dATP (1000 Ci/mmol; Amersham). Universal oligonucleotide primers (SK, KS, T3, T7 and M13rev; Stratagene) were used to determine the sequence of the first and last 300 nucleotides in each the subcloned fragment. Based on the nucleotide sequences of the sense strand and the antisense strand of the genomic fragment, two oligonucleotides that were each 18 nucleotides in length were synthesized on an Applied Biosystems 380A Oligonucleotide Synthesizer at the Harvard Microchemistry Facility, Cambridge, Ma. These oligonucleotides were then used as primers to determine the contiguous nucleotide sequence of the next 200-250 nucleotides in each direction of the double stranded DNA. Additional oligonucleotides complementary to different regions of the cDNA were used as primers to extend the sequence from the exons in both directions. Nucleotide sequence data was entered and edited on an IBM-PC using the Clatech molecular biology software package. Data base searches and homology comparisons with the mouse secretory granule proteoglycan peptide core gene and other genes were performed using the computers at the Molecular Biology Computer Research Resource at Dana-Farber Cancer Institute, Boston, Ma.

When a human genomic library was screened using the entire 650 bp cDNA-H4 probe, six independent clones were isolated (designated as λHG-PG1 to λHG-PG6). Restriction mapping of these clones revealed that all six of the clones lacked a 5' 12 kb EcoRI→EcoRI fragment and failed to hybridize to a 136 bp 5'→KpnI fragment of cDNA-H4. Rescreening of the genomic library with the 5' fragment of cDNA-H4 resulted in the isolation of two additional clones that were designated as λHG-PG7 and λHG-PG8, respectively. When analyzed by restriction mapping, clones λHG-PG6, λHG-PG7, and λHG-PG8 contained overlapping genomic sequences which taken together include the entire gene which encodes the human secretory granule proteoglycan peptide core.

Detailed restriction mapping of these subclones revealed that this gene spans at least 15 kb and consists of 3 exons. Between the first and second exon is an approximate 8 kb intron, and between the second and third exon is an approximate 6 kb intron. Both introns begin with the nucleotide sequence "GTAAG" and end with the sequence "CAG". Analysis of the nucleotide sequence of this gene revealed that exon 1 encodes the 5' untranslated region of the mRNA transcript and the entire 27 amino acid hydrophobic signal peptide of the translated molecule. Exon 2 encodes a 49 amino acid portion of the peptide core (amino acid residues 28 to 76) which would be predicted to be the N-terminus of the molecule after the hydrophobic signal peptide is removed in the endoplasmic reticulum. Exon 3 (634 bp) is the largest exon and encodes the remaining 82 amino acids of the translated molecule and the entire 3' untranslated region of the mRNA transcript. These 82 amino acids encode a 17 amino acid sequence (residues 77 to 93) that immediately precedes the serine-glycine rich glycosaminoglycan attachment region, the 18 amino acid serine-glycine rich region (residues 94 to 111), the C-terminus of the translated molecule (residues 112 to 158).

Determination of the Transcription-Initiation Site of the Human Secretory Granule Proteoglycan Peptide Core Gene. A S1 nuclease mapping analysis was performed to identify the transcription-initiation site of the human gene that encodes the peptide core of secretory granule proteoglycans in HL-60 cells. A 4 kb SalI→HindIII fragment of the genomic clone λHG-PG7 was subcloned into Bluescript (designated pB5SH3). An oligonucleotide (5'043 ACTGCAM GAG-TAGCTT→3') was synthesized that corresponded to the residues 39 to 59 of the antisense strand of cDNA-H4. Ten nanograms of this oligonucleotide were hybridized to 4 μg of alkali-denatured pB5SH3, and a complementary strand of DNA was synthesized under conditions similar to that described above except that it was labeled with [α-$^{32}$P]dATP. A 400 bp antisense DNA probe was isolated following electrophoresis of the synthetic product on a denaturing 8M urea/8% polyacrylamide gel. The single-stranded radiolabeled DNA fragment was identified by autoradiography, electroeluted, and ethanol precipitated. A 50,000 cpm sample of the radiolabeled DNA fragment was hybridized to ~15 μg of HL-60 cell-derived total RNA (Chirgin, J. M. et al., Biochemistry 18:5294-5299 (1979)) or 1 μg of HL-60 cell-derived poly(A)+ RNA (Aviv, H. et al., Proc. Natl. Acad. Sci. U.S.A. 69:1408-1412 (1972)) at 48° C. for 16 h in 80% formamide, 400 mM NaCl, 1 mM EDTA, and 40 mM Pipes (pH 6.4). The $^{32}$P-DNA/RNA hybrid was incubated with 100 U of S1 nuclease (Pharmacia) for 60 min. At the end of the reaction, the sample was extracted with phenol, and ethanol precipitated at −80° C. Three microliters of 1 mM EDTA and 10M Tris-HCl (pH 8.0) and 4 μl of formamide loading buffer were added to the precipitated sample. The sample was boiled, and loaded onto a 8M urea/8% polyacrylamide sequencing gel along side a MI digest of $^{32}$p-labeled pBR322 (New England Biolabs) and a sequencing ladder of pBSH3 that had been primed with the same oligonucleotide. For two negative controls, S1 nuclease reactions were concurrently preformed with 15 μg of tRNA (Bethesda Research Labs) or MBBC (Razin, E. et al., J. Biol. Chem. 257:7229-7236 (1982)) total RNA.

HL-60 cell-derived total RNA and poly(A)+ RNA protected ~82 nucleotides of the probe from degradation by S1 nuclease. Therefore, it was concluded that the putative transcription-initiation site In HL-60 cells for this gene resided 53 bp upstream of the translation-initiation site. The $^{32}$P-labeled 5' antisense 400 bp DNA fragment was not protected if it was incubated with tRNA or mouse mast cell RNA prior to exposure to S1 nuclease. This deduced transcription-initiation site in HL-60 cells corresponds to the deduced transcription-initiation site of the analogous gene that is expressed in BMMC-derived mast cells and rat basophilic leukemia cells (Bourdon, M. A. et al., Mol. Cell Biol. 7:33-40 (1987)), but not in rat L2 yolk sac tumor cells (Bourdon, M. A. et al., Mol. Cell Biol. 7:33-40 (1987)).

Figure 3:
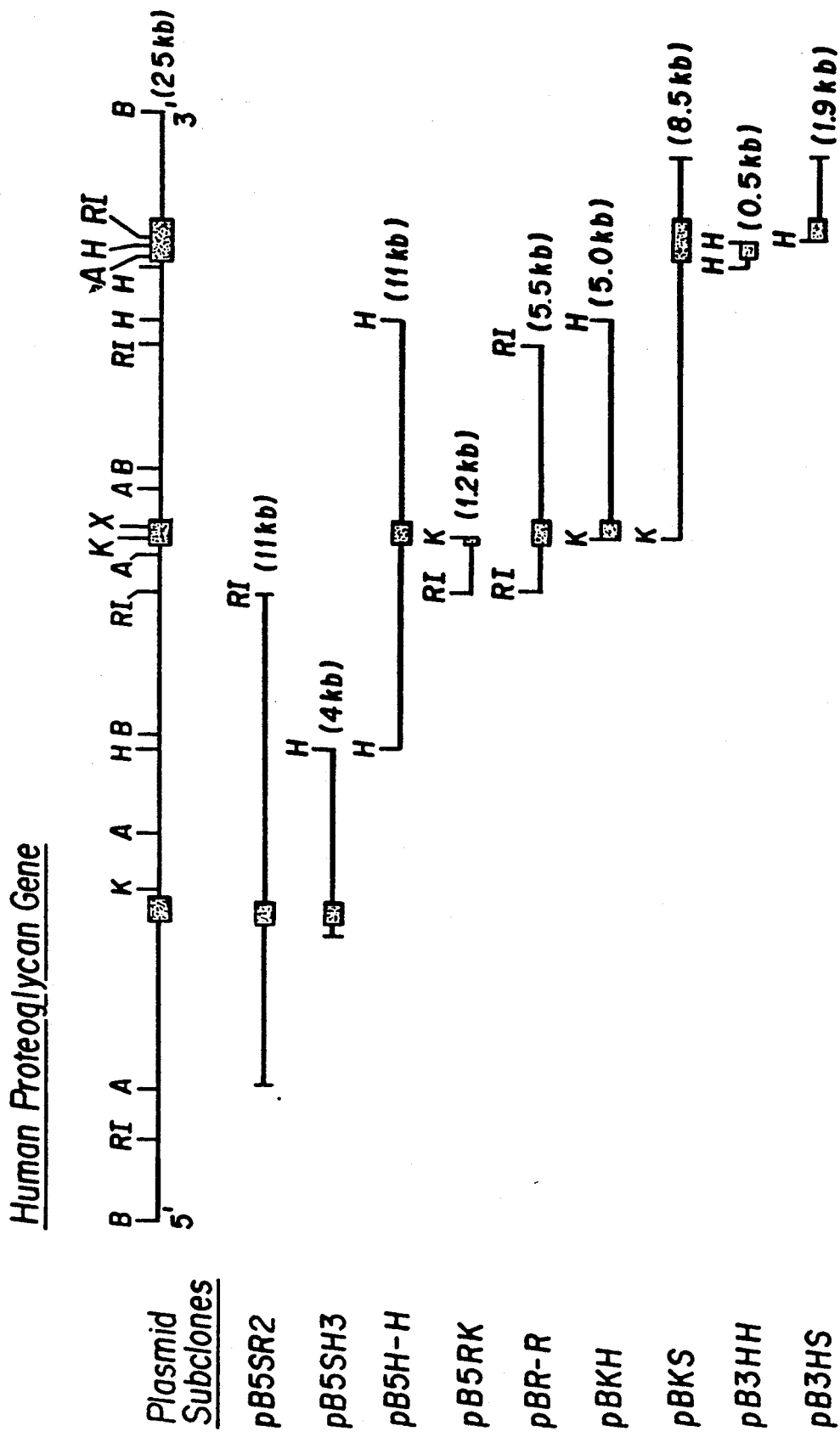
FIG. 3. Restriction map of the human secretory granule proteoglycan peptide core gene isolated from a human leukocyte genomic DNA library (Klickstein, L. B. et al., *J. Exp. Med.* 165:1095–1112 (1987)).

FIG. 3 is a restriction map of the human gene. FIG. 4 is the nucleotide sequence of the gene that encodes the human secretory granule proteoglycan peptide core protein including flanking and intron sequences.

Cloning of the Mouse Gene. A 15 kb mouse genomic fragment containing the gene that encodes the mouse secretory granule proteoglycan peptide core protein was cloned by screening a mouse genomic library derived from a Sau3AI digest of BALB/c mouse liver DNA (Avraham, S., et al., Proc. Natl. Acad. Sci. U.S.A/ 8-6:3763-3767 (1989)), using a [α-$^{32}$P]dCTP labeled 450 bp AccI→3' gene-specific fragment of a BMMC cDNA (cDNA-M6) that encodes the peptide core of mouse secretory granule proteoglycan using methods as described above. The nucleotide sequence and the deduced amino acid sequence of this gene is presented in FIG. 5.

Neither the human nor the mouse gene have a classical TATA box (Breathnach, R. et al., Ann. Rev. Biochem. 50:349-383 (1981)) or GC-rich element (Sehgal, A. et al., Mol. Cell. Biol. 8:3160-3167 (1988)) ~30 bp upstream of its transcription-initiation site. Therefore, it is likely that the secretory granule proteoglycan peptide core gene that is expressed in hematopoietic cells has an unusual promoter. The 5' flanking region has not been described for any other human proteoglycan peptide core gene, and thus comparisons with genes that encode other proteoglycan peptide cores cannot yet be made. However, there are several nucleotide sequences within these 5' flanking areas of the human and mouse secretory granule proteoglycan peptide core genes that are identical to several known cis acting regulatory elements for other genes. Of importance is the finding that 96% of the nucleotides that are present in a 119 bp nucleotide sequence just upstream of the transcription-initiation site of the human (residues −1 to −119) and mouse (residues −1 to −123) gene are identical. This degree of conservation greatly exceeds that obtained when any other 119 bp region within the exons of the gene in these two species is compared, and suggests that important cis acting regulatory elements are present in this conserved nucleotide sequence.

EXAMPLE 5

Transfection of Rat-1 Fibroblasts with the Mouse Secretory Proteoglycan Peptide Core Gene. Fisher rat-1 fibroblasts were grown in Dulbecco's modified essential medium (DMEM) supplemented with 10% fetal calf serum, 2 mM L-glutamine, 100 U/ml of penicillin, and 100 µg/ml of streptomycin, at 37° C. in a humidified atmosphere of 5% $CO_2$. DNA cotransfections were performed essentially as described elsewhere (Southern, P. J. et al., *J. Mol. Appl. Gen.* 1:327–341 (1982)). In brief, 3–4×$10^5$ rat-1fibroblasts were placed into each 10-cm plastic culture dish containing DMEM for 12–24 h before cotransfection with the mouse genomic clone λMG-PG1 and the selectable maker pSV2 neo. A calcium phosphate/DNA precipitate was created by adding 0.5 ml of a 250-mM solution of calcium phosphate containing 5 µg of the λMG-PG1 DNA and 0.5 µg of pSV2 neo drop-wise in the presence of bubbling air to 0.5 ml of 280 mM NaCl, 10 mM KCl, 12 mM dextrose, 1.5 mM sodium phosphate, and 50 mM HEPES (pH 7.1). The precipitate that formed after a 30 min incubation was added to a culture dish of fibroblasts, and 10 to 18 h later, the DNA precipitate was removed. The transfected cells were washed twice with growth medium and then were allowed to recover for 24 h before being trypsinized and split at a ratio of 1:6. The resulting fibroblasts were plated into new 10-cm plastic dishes and cultured for 2 to 3 wk in DMEM containing 500 µg/ml gentamicin (Gibco); the culture medium was changed every 3 days. At the end of this period, gentamicin-resistant colonies of transfected fibroblasts were individually picked with cloning cylinders and grown as cell lines in culture medium containing 100 µg/ml gentamicin.

RNA and DNA Blot-Analysis of Rat-1 Fibroblasts Transfected with the Mouse Proteoglycan Gene. Total RNA was prepared from mouse BMMC, rat-1 fibroblasts, and transfected rat-1 fibroblasts by a guanidinium thiocyanate method (Chirgin, J. M. et al., *Biochemistry* 18:5294–5299 (1979); Glisin, V. et al., *Biochemistry* 13:2633–2637 (1974)). RNA (5 µg/lane) was electrophoresed in 1% formaldehyde-agarose gels, and transferred to Zetabind (Thomas, P. S., *Proc. Natl. Acad. Sci, U.S.A.* 77:5201–5205 (1980)). The resulting RNA blots were incubated at 42° C. for 24 h in hybridization buffer containing a radiolabeled AccI→3' fragment of cDNA-M6. The blots were washed under conditions of high stringency, and autoradiography was performed. The proteoglycan peptide core probe was removed from the blots by high temperature washing, and the blots were reprobed with an actin cDNA to quantitate the amount of mRNA that had been loaded in each lane.

DNA was isolated (Blin, N. et al., *Nucleic Acids Res.* 3:2303–2308 (1976)) from the mouse liver, rat liver, rat-1 fibroblasts, and transfected rat-1 fibroblasts, and samples were digested (10 µg/digest) separately with XmnI, BamHI, BglII, SspI, Sau3AI, HindIII, or EcoRI for 4 h at 37° C. The fragments were resolved by agarose gel electrophoresis and were transferred to Zetabind. The resulting DNA blots were analyzed for hybridization under conditions of high stringency with the AccI→3' fragment of the mouse cDNA-M6 as a probe.

Expression of the Mouse Gene that Encodes the Peptide Core of Mouse Secretory Granule Proteoglycans in Transfected Rat-1 Fibroblasts. To demonstrate that λMG-PG1 contained the entire mouse secretory granule proteoglycan peptide core gene, including its promoter region, and that this mouse genomic clone could be expressed in another mammalian cell, rat-1 fibroblasts were cotransfected with λMG-PG1 and the dominant neo-resistant selectable marker encoded by the plasmid pSV2 neo. Seventeen independent clones of neo-resistant transfected rat-1 fibroblasts were isolated and were expanded separately. Total RNA was isolated from BMMC, neo-transfected rat-1 fibroblasts, and the cotransfected rat-1 fibroblast cell lines.

The gene-specific secretory granule proteoglycan peptide core probe failed to hybridize to any transcript in RNA blots of nontransfected fibroblasts; however, it did hybridize to a 1.0-kb RNA transcript in mouse BMMC and in two of the cotransfected rat-1 fibroblast cell lines. Primer extension analyses were performed using RNA from the transfected fibroblasts to determine the transcription-initiation site. When RNA from the transfected cells was used as an RNA template, ∼80 nucleotides were extended onto the oligonucleotide primer that corresponded to residues 78 to 98 of cDNA-M6, resulting in a DNA product of −100 nucleotides in length. A DNA product of ∼60 nucleotides was obtain when the alternative primer that corresponded to residues 39 to 59 of cDNA-M6 was used in the assay.

Genomic DNA was prepared from the above two clones of transfected rat-1 fibroblasts, and was digested with BglII, XmnI, SAlI, or BamHI. DNA blots of the digests were probed with the AccI→3' gene-specific fragment of cDNA-M6 to demonstrate that these transfected rat-1 fibroblast cell lines contained in mouse proteoglycan genomic sequences. The mouse proteoglycan probe hybridized to a 2.7-kb fragment present in the BglII digest of mouse live DNA, and to a 7.5-kb fragment in the BglII digests of both rat liver DNA and rat-1 fibroblast DNA. The transfected fibroblasts differed from the nontransfected rat-1 fibroblasts in that they contained both the 2.7-kb and the 7.5-kb DNA fragments. Based on the relative intensity of hybridization of the gene-specific probe to the 2.7-kb fragment present in the BglII digests of equal amounts of mouse liver DNA and fibroblast DNA, the fibroblast cell lines may have incorporated 10–20 and 2–3 copies, respectively, of the mouse secretory granule proteoglycan peptide core gene into their genome.

Transfections have been performed in Chinese hamster ovary cells with a cDNA that encodes the peptide core of the fibroblast-derived dermatan sulfate proteoglycan called decorin (Yamaguchi, Y. et al., *Nature* 336:244–246 (1988)) and in COS-7 cells with a cDNA that encodes the peptide core of the T-cell derived invariant chain proteoglycan that associates with Ia (Miller, J. et al., *Proc. Natl. Acad. Sci. U.S.A.* 85:1359-1363 (1988)), but no transfections have been reported using a genomic clone that contains an entire proteoglycan peptide core gene.

EXAMPLE 6

Preparation of Antibodies to Peptides of the Amino Acid Consensus Sequence Which Recognize Native HL-60 Secretory Granule Proteoglycan Peptide Core Protein. A 16 amino acid peptide 02 [Ser-Asn-Lys-Ile-Pro-Arg-Leu-Arg-Thr-Asp-Leu-Phe-Pro-Lys-Thr-Arg] was chemically synthesized, coupled to hemocyanin, and injected into a New Zealand White rabbit. This peptide corresponds to residues 64-79 of the translated molecule and was a region of the core that preceded the serine-glycine rich glycosaminoglycan attachment region.

The induction of antibodies which specifically recognize the peptide core protein of human secretory granule proteoglycan was tested as follows. The peptide (3 mg) was coupled with 5 mg of Keyhole Limpet hemocyanin (Sigma) in the presence of 0.25% glutaraldehyde, and polyclonal antibodies were raised to the coupled peptide in New Zealand White rabbits using standard immunization methodologies. Antibody titers in whole sera were measured using an enzyme linked immunosorbent assay (ELISA). Each microtiter well was incubated overnight at 4° C. with 1 μg of synthetic peptide in phosphate buffered saline. After the remaining protein binding sites in the wells were blocked by a 1 h incubation with 1% (w/v) bovine serum albumin (Sigma), the wells were washed with phosphate buffered saline containing 1% (w/v) Tween 20. Rabbit sera that was serially diluted in phosphate buffered saline was added, followed by horseradish peroxidase-conjugated goat anti-rabbit IgG (Bio-rad, Richmond, Calif.); the wells were then assayed spectrophotometrically for development of the 2,2′azino-di-[3-ethyl-benzthiazoline sulfonate] dye (Boehringer-Mannheim, Indianapolis, Ind.). Peptide 01 (Ser-Val-Gln-Gly-Tyr-Pro-Thr-Gln-Arg-Ala-Arg-Tyr-Gln-Trp-Val-Arg) that corresponded to residues 24 to 39 of the deduced amino acid of cDNA-H4 was also synthesized and used in the ELISA to confirm the specificity of the rabbit antisera. Anti-peptide IgG was partially purified by ammonium sulfate precipitation followed by ion exchange chromatography.

Anti-peptide IgG (~30 μg) was incubated with 100 μl of a 15% (w/v) suspension of the Protein A-Sepharose beads (Sigma) in RIPA buffer for 1 h at room temperature. The resulting Protein A-Sepharose-IgG complex was added to 1 ml of RIPA cell lysates containing $5 \times 10^6$ cell equivalents of [$^{35}$S]methionine-labeled or [$^{35}$S]sulfate-labeled HL-60 cells that had been precleared by incubation for 24 h with Protein A-Sepharose alone and then for 24 h with Protein A-Sepharose/preimmune IgG. After a 18-24 h incubation at 4° C. with Protein A-Sepharose/anti-peptide IgG, the beads were washed 3 times by centrifugation with 0.1% bovine serum albumin, 0.5% Tween 20, and 10 mM phosphate buffered saline (pH 7.2) containing either 10 mM unlabeled methionine or unlabeled sodium sulfate. The bound radiolabeled antigens were eluted by suspending the beads in 60 μl of Laemmli buffer and incubating for 5 min at 95° C. The eluates were electrophoresed in 15% SDS-PAGE gels, stained with Coomassie Brilliant blue, dried, and autoradiographed using Kodak XAR-5 film.

Figure 6:
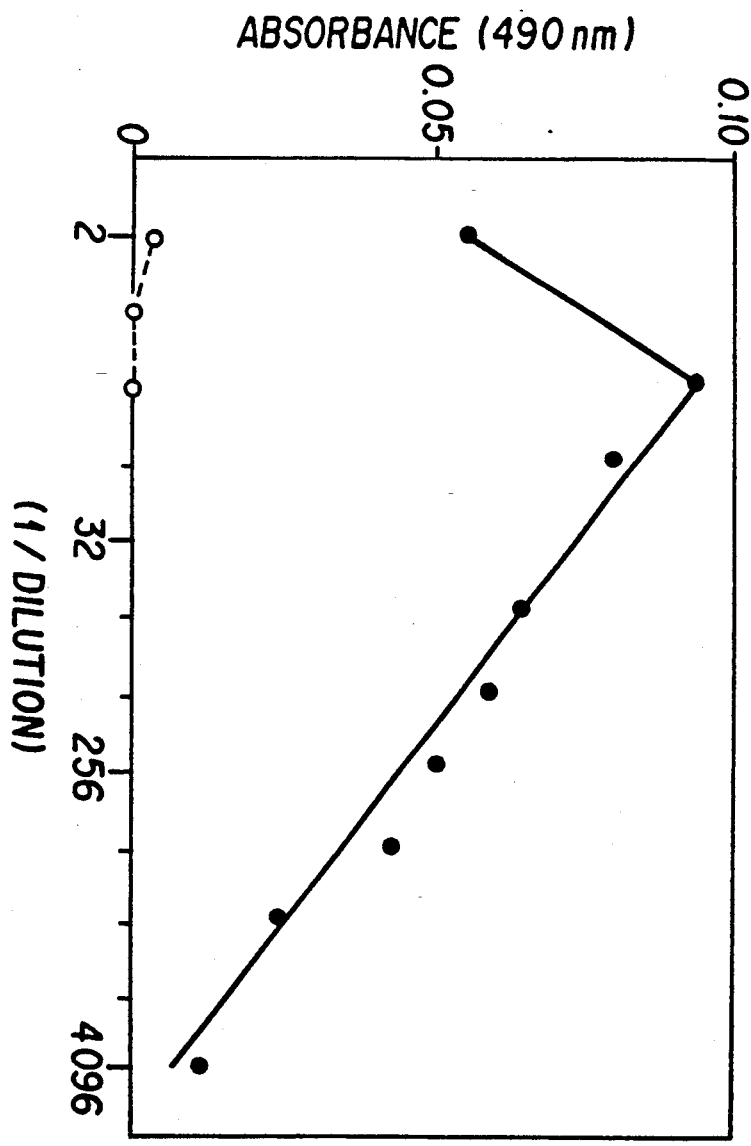
FIG. 6. ELISA of the rabbit anti-peptide 02 serum. Peptides 01 (O---O) and 02 (●---●) were coupled to separate microtiter wells and different dilutions of the rabbit anti-peptide 02 sera were examined for their reactivity against the specific peptide as detected spectrophotometrically at 490 nm after the addition of horseradish peroxidase-conjugated goat anti-rabbit antibody followed by 2,2'azino-di-[3-ethyl-benzthiazoline] sulfonate.

In the ELISA, the antiserum gave half-maximal binding at an approximate 500 fold dilution (FIG. 6). The anti-peptide 02 serum failed to recognize peptide 01 which corresponded to deduced amino acid residues 24 to 39 of the same cDNA (FIG. 6). The preimmune sera also failed to react with the coupled peptide 02. When 1 μl of the antisera was preincubated with 1 μg of peptide 02 for 60 minutes at 25° C., no immunoreactivity was detected in the ELISA.

An IgG-enriched fraction of the anti-peptide 02 sera was used to determine if Protein A-Sepharose-bound antibodies would recognize the initially-translated secretory granule peptide core and the mature proteoglycan. A prominent 20,000 $M_r$ protein was specifically immunoprecipitated from lysates of 2 min [$^{35}$S]methionine-labeled HL-60 cells, whereas both a 20,000 $M_r$ protein and a macromolecule that barely entered the gel were specifically immunoprecipitated from 10 min radiolabeled cells. After a 10 min pulse and a 5 min chase, the 20,000 $M_r$ [$^{35}$S]methionine-labeled protein was less apparent while the macromolecule was somewhat increased. The [$^{35}$S]methionine-labeled macromolecule corresponded in size exactly to the [$^{35}$S]sulfate-labeled proteoglycan that was precipitated after an overnight radiolabeling of the cells with $^{35}$S]sulfate. Because precipitation was inhibitable by preincubation of the Protein A-Sepharose-immune IgG with 1 μg of the synthetic peptide 01, it was concluded that the rabbit anti-peptide 02 antibodies recognize the precursor and mature HL-60 cell proteoglycan peptide core.

Figures 7A, 7B:
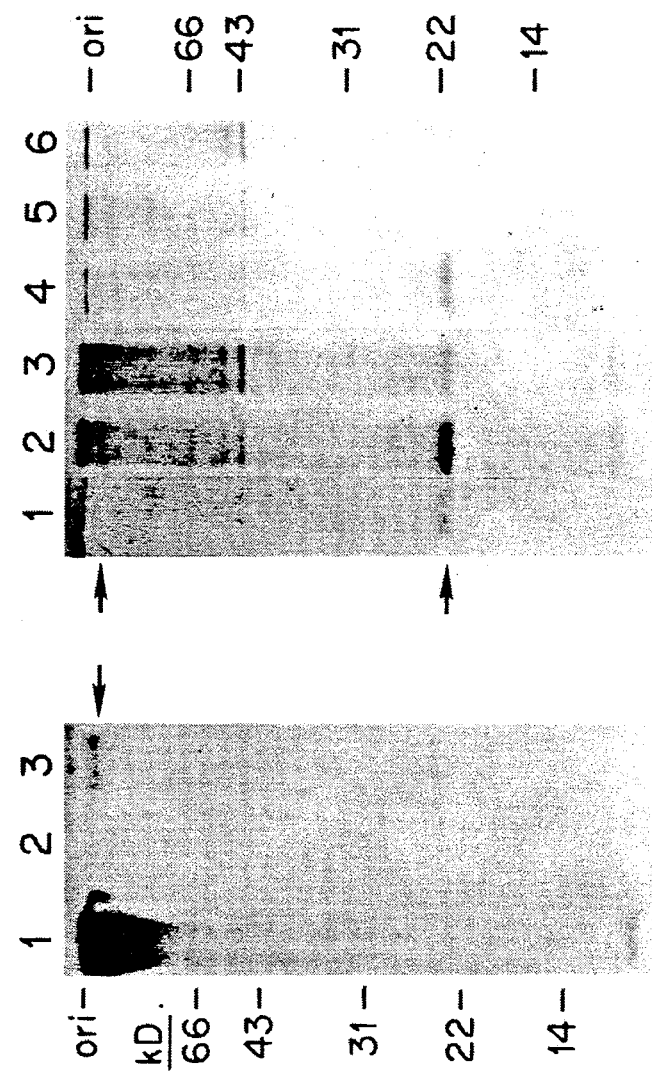
FIGS. 7A&B SDS-PAGE analysis of immunoprecipitates of lysates of [$^{35}$S]sulfate-labeled (7A) and [$^{35}$S]methionine-labeled (7B) HL-60 cells. (7A) Lysates of [$^{35}$S]sulfate-labeled HL-60 cells were analyzed before (lane 1) and after immunoprecipitation with anti-peptide 02 IgG in the presence (lane 2) or absence (lane 3) of peptide 02. (7B) Lysates of HL-60 cells were analyzed after a 2 min (lane 1) or a 10 min (lane 2) incubation with [$^{35}$S]methionine by immunoprecipitation with anti-peptide 02 IgG. Ten min [$^{35}$S]methionine-labeled HL-60 cells were washed and then incubated for an additional 5 min in methionine-containing enriched medium before lysates were immunoprecipitated with anti-peptide 02 IgG (lane 3). Lysates of 5 min labeled HL-60 cells were imunoprecipitated with anti-peptide 02 IgG in the presence of peptide 01 (lane 4) or peptide 02 (lane 5). The [$^{35}$S]methionine-labeled proteins that were nonspecifically immunoprecipitated with pre-immune IgG are depicted in lane 6. The origin (ori) and the $M_r$ markers are indicated on the far left and right of each panel. The arrows indicate the precursor peptide core and the mature proteoglycan that are imunoprecipitated with anti-peptide 02 IgG.

As shown in FIG. 7, the size of the immunoprecipitated peptide core protein was approximately 13,000 daltons, consistent with the size predicted by Stevens et al., *J. Biol. Chem.* 263:7287 (1988) for the peptide core which has lost its 27 amino acid signal peptide.

EXAMPLE 7

Isolation of Proteoglycan Protein

Human proteoglycan peptide core protein can be isolated using common protein isolation techniques known in the art such as column chromatography, gel electrophoresis, affinity chromatography, or immunoextraction techniques using the antibody described above. For example, such proteoglycans may be extracted by the following procedure (Stevens, R. L., et al., *J. Biol. Chem.* 260:14194-14200 (1985)).

BMMC pellets are lysed by resuspension for 30 s in 50 μl of 1% Zwittergent 3-12 containing protease inhibitors, followed by the addition of 2.35 ml of 4M guanidine HCl (GnHCl) containing CsCl (density 1.4 g/ml). These detergent-GnHCl proteoglycan extracts are then pooled such that in a typical experiment 48 ml of extract is obtained from approximately $2 \times 10^9$ BMMC, of which $3 \times 10^7$ are radiolabeled. The pooled extracts are centrifuged at 17° C. for 48 h at 95,000×g, and the gradients are divided in most experiments into two equal fractions termed $D_1$ (bottom) and $D_2$ (top), respectively. The distribution of chondroitin sulfate E proteoglycan in fractions from the CsCl gradient or from subsequent ion exchange or gel filtration chromatography is determined by suspending a sample of each fraction in 12.5 ml of Hydrofluor and quantitating $^{35}$S or $^3$H radioactivity in the radiolabeled proteoglycan on a Tracor Analytic Mark III liquid scintillation counter. Protein is detected by the method of Lowry et al. with bovine serum albumin as a standard or by optical density at 280 nm. Nucleic acids are detected at a wavelength of 260 nm. The bottom fraction of each CsCl gradient is placed in dialysis tubing of 50,000 $M_r$ cut-off and dialyzed at 4° C. against 1M NaCl for 24 h and then for an additional 24 h against 1M urea containing 0.05M Tris-HCl, pH 7.3. The dialysate is adjusted to 4M in urea by the addition of solid urea and applied to a 0.8×29-cm column of DEAE-52 previously equilibrated in 4M urea, 0.05M Trim-HCl, pH 7.8. The ion exchange column is washed with 35 ml of 4M urea, 0.05M Trim-HCl, pH 7.8, and the chondroitin sulfate E proteoglycan eluted with a 180-ml linear gradient of NaCl (0–1.0M) in the urea buffer at a flow rate of 4 ml/h. Two-ml fractions are collected, and the proteoglycan-enriched fractions, detected by monitoring a portion of the fraction for either $^{35}$S or $^3$H radioactivity if the cells have been prelabelled, are pooled, dialyzed 48 h at 4° C. against 0.1M NH$_4$HCO$_3$, and lyophilized. This material is redissolved in 100 µl of 4M GnHCl/0.1M sodium sulfate/0.1M Tris-HCl, pH 7.0, applied to a 0.6×100-cm column of Sepharose CL-4B in this same buffer, and eluted from the column at a flow rate of 1.5 ml/h. One-half ml fractions are collected and analyzed for radioactivity and absorbance at 280 nm. The proteoglycan-containing fractions are pooled, dialyzed against 0.1M NH$_4$HCO$_3$ and lyophilized.

EXAMPLE 8

Isolation and Protease-Resistance of HL-60 Cell Proteoglycan

Radiolabeling of HL-60 Cells——HL-60 cells (line CCL 240; American Type Culture Collection, Bethesda, Md.) were cultured in enriched medium [RPMI-1640 medium supplemented with 10% (v/v) fetal calf serum, 2 mM L-glutamine, 0.1 mM nonessential amino acids, 100 U/ml of penicillin, and 100 µg/ml of streptomycin (Gibco, Grand Island, N.Y.)] at 37° C. in a humidified atmosphere of 5% CO$_2$. For [$^{35}$S] methioninelabeling, HL-60 cells were preincubated at a concentration of 10$^7$ cells/ml for 10 min in methionine-free, enriched medium containing dialyzed fetal calf serum. Approximately 500 µCi/ml of [$^{35}$S]methionine (129 Ci/mmol; Amersham, Arlington Heights, Ill.) was then added. The HL-60 cells were incubated for an additional 2 to 10 min at 37' C., centrifuged in the cold at 120×g, and washed at 4° C. in enriched medium. In the pulse-chase experiments, HL-60 cells were [$^{35}$S]methionine-labeled for 10 min, were washed as above, and were resuspended in normal enriched medium at 37° C. for an additional 5 min. Aliquots of 5×10$^6$ [$^{35}$S]methionine-labeled HL-60 cells were lysed in 1 ml of RIPA buffer [0.15M NaCl, 1% deoxycholate, 1% Nonident P-40, 0.1% SDS, 10 mM N-ethylmaleimide, 2 mM phenylmethylsulfonyl fluoride, 10 mM NaF, and 0.1M Trim-HCl, pH 7.2], and immunoprecipitates of the lysates were analyzed by SDS-polyacrylamide gel electrophoresis (SDS-PAGE) as described below.

For [$^{35}$S]Sulfate labeling, HL-60 cells were incubated in enriched medium containing 50 µCi/ml of [$^{35}$S]sulfate (~4000 Ci/mmol; DuPont-New England Nuclear, Boston, Ma.) for 1 h at a density of 1×10$^7$ cells/ml or for 18 h at a density of 2×10$^6$ cells/ml. The radiolabeled cells were centrifuged at 4° C. for 10 min at 120×g, and 150 µl of 1% (w/v) zwittergent 3-12 (Calbiochem, San Diego, Calif.) containing 100 µg of chondroitin sulfate A (Miles Scientific, Naperville, Ill.) and 100 µg of heparin (Sigma, St. Louis, Mo.) glycosaminoglycan carriers were added to each cell pellet followed by 1.35 ml of 4M GNHCl, 0.1M sodium sulfate, and 0.1M Tris-HCl. A sample of each lysate and supernatant was chromatographed on Sephadex G-25/PD-10 columns (Phamacia, Piscataway, N.J.) to quantitate the incorporation of [$^{35}$S]sulfate into macromolecules.

In order to isolate the [$^{35}$S]sulfate-labeled HL-60 cell proteoglycans, solid CsCl was added to the remainder of the cell lysates to achieve final densities of 1.4 g/ml. Following centrifugation for 48 h at ~100,000×g, the bottom 33% of each CsCl gradient was dialyzed sequentially against 0.5M sodium acetate for 24 h and 0.1M ammonium bicarbonate for an additional 24 h. The dialysates were lyophilized and redissolved in 0.4 ml of water. Samples of partially purified [$^{35}$S]sulfate-labeled proteoglycans were incubated for 30 min with or without 10 µg of Pronase (Calbiochem), and the digests were applied sequentially to a 0.8×85 cm column of Sepharose CL-6B (Pharmacia) that had been equilibrated with 4M GNHCl, 0.1M sodium sulfate, 0.1M Trim-HCl, pH 7.2. As a control, samples of [$^{35}$S]sulfate-labeled chondrosarcoma proteoglycans were analyzed in parallel for their susceptibility to Pronase. Pronase-sensitive chondrosarcoma proteoglycans are extracellular matrix proteins and are distinguished from secretory granule proteoglycans.

No substantial change in the hydrodynamic size of the HL-60 cell [$^{35}$S]Sulfate-labeled proteoglycans was detected following Pronase treatment, whereas rat [$^{35}$S]sulfate-labeled chondrosarcoma proteoglycans were susceptible to degradation. These results show that the proteoglycan was resistant to Pronase digestion.

While this invention has been described in detail and with reference to specific embodiments thereof, it will be apparent to one skilled in the art that various changes and modifications could be made therein without departing from the spirit and scope thereof.

We claim:
1. A peptide of the formula SVQGYPTQRARYQWVR.
2. A peptide of the formula SNKIPRLRTDLFPKTR.

* * * * *